(12) United States Patent
Nistor et al.

(10) Patent No.: US 11,672,843 B2
(45) Date of Patent: Jun. 13, 2023

(54) SOMATOSTATIN RECEPTOR AGONIST FORMULATIONS

(71) Applicant: CAMURUS AB, Lund (SE)

(72) Inventors: Catalin Nistor, Lund (SE); Markus Johnsson, Lund (SE); Fredrik Tiberg, Lund (SE)

(73) Assignee: CAMURUS AB, Lund (SE)

( * ) Notice: Subject to any disclaimer, the term of this patent is extended or adjusted under 35 U.S.C. 154(b) by 0 days.

(21) Appl. No.: 14/401,559

(22) PCT Filed: May 24, 2013

(86) PCT No.: PCT/EP2013/060739
§ 371 (c)(1),
(2) Date: Feb. 13, 2015

(87) PCT Pub. No.: WO2013/174978
PCT Pub. Date: Nov. 28, 2013

(65) Prior Publication Data
US 2015/0105332 A1    Apr. 16, 2015

Related U.S. Application Data

(63) Continuation of application No. PCT/EP2012/059917, filed on May 25, 2012.

(60) Provisional application No. 61/730,613, filed on Nov. 28, 2012.

(51) Int. Cl.
| | |
|---|---|
| A61K 38/12 | (2006.01) |
| A61K 38/08 | (2019.01) |
| A61K 9/00 | (2006.01) |
| A61K 38/31 | (2006.01) |
| C07K 5/00 | (2006.01) |
| C07K 7/00 | (2006.01) |
| C07K 16/00 | (2006.01) |
| C07K 17/00 | (2006.01) |
| A61K 38/04 | (2006.01) |
| A61K 47/10 | (2017.01) |
| A61K 47/14 | (2017.01) |
| A61K 47/24 | (2006.01) |
| A61K 31/4045 | (2006.01) |
| A61K 9/127 | (2006.01) |
| C07K 7/64 | (2006.01) |
| A61K 47/18 | (2017.01) |

(52) U.S. Cl.
CPC ............ *A61K 38/12* (2013.01); *A61K 9/0019* (2013.01); *A61K 9/0024* (2013.01); *A61K 9/1274* (2013.01); *A61K 31/4045* (2013.01); *A61K 38/08* (2013.01); *A61K 38/31* (2013.01); *A61K 47/10* (2013.01); *A61K 47/14* (2013.01); *A61K 47/24* (2013.01); *C07K 7/64* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 4,938,763 | A | 7/1990 | Dunn et al. |
| 5,340,802 | A | 8/1994 | Shiosaki et al. |
| 5,480,656 | A | 1/1996 | Okada et al. |
| 5,531,925 | A | 7/1996 | Landh et al. |
| 5,639,480 | A | 6/1997 | Bodmer et al. |
| 5,776,885 | A | 7/1998 | Orsolini et al. |
| 5,807,573 | A | 9/1998 | Ljsuberg-Wahren et al. |
| 5,955,502 | A | 9/1999 | Hansen et al. |
| 6,011,067 | A | 1/2000 | Hersh |
| 6,066,328 | A | 5/2000 | Ribier et al. |
| 6,113,943 | A | 9/2000 | Okada et al. |
| 6,228,383 | B1 | 5/2001 | Hansen et al. |
| 6,458,924 | B2 | 10/2002 | Knudsen et al. |
| 6,464,987 | B1 | 10/2002 | Fanara et al. |
| 7,473,761 | B2 * | 1/2009 | Albert ............... C07K 7/64 530/317 |
| 8,097,239 | B2 | 1/2012 | Johnsson et al. |

(Continued)

FOREIGN PATENT DOCUMENTS

| | | |
|---|---|---|
| CA | 2535463 A1 | 1/1991 |
| EP | 1600162 A1 | 11/2005 |

(Continued)

OTHER PUBLICATIONS

"Somatostatin analogue shows promise in Cushing's disease," Nature Rev. 9:830 (2010).*
Cambridge Isotope Laboratories, Inc., "Calculating Concentrations of Free Acid or Base from Salt Form," available online at http://www.isotope.com/userfiles/files/assetLibrary/ENV_NEWS_ACID_calculating.pdf, 1 page (2014).*
Sengwa, et al., J. Molec. Liquids 108:47-60, (2003) (Year: 2003).*
N. Ardjomand et al., "Expression of Somatostatin Receptors in uveal melanomas," Inv. Opthalmol. & Vis. Sci., 2003, vol. 44, No. 3, pp. 980-987.

(Continued)

*Primary Examiner* — Thea D'Ambrosio
(74) *Attorney, Agent, or Firm* — Raphael Bellum PLLC

(57) ABSTRACT

The present invention relates to compositions forming a low viscosity mixture of: a) 20-50 wt. % of at least one diacyl glycerol; b) 20-54 wt. % of at least one phosphatidyl choline (PC); c) 5-15 wt. % of at least one biocompatible, organic mono-alcoholic solvent; d) 1 to 20 wt. % polar solvent e) 5 to 150 mg/ml of at least one peptide somatostatin receptor agonist comprising pasireotide; f) optionally at least one antioxidant; wherein the ratio of components a:b is in the range 40:60 to 54:46; wherein the pre-formulation forms, or is capable of forming, at least one liquid crystalline phase structure upon contact with excess aqueous fluid. The invention further relates to methods of treatment comprising administration of such compositions, and to pre-filled administration devices and kits containing the formulations.

29 Claims, 7 Drawing Sheets

Specification includes a Sequence Listing.

(56) References Cited

U.S. PATENT DOCUMENTS

| | | | |
|---|---|---|---|
| 8,182,834 B2 | 5/2012 | Johnsson et al. | |
| 8,187,629 B2 | 5/2012 | Barauskas et al. | |
| 8,236,292 B2 | 8/2012 | Thuresson et al. | |
| 8,236,755 B2 | 8/2012 | Thuresson et al. | |
| 9,526,788 B2* | 12/2016 | Johnsson | A61K 9/127 |
| 9,555,118 B2* | 1/2017 | Tiberg | A61K 9/0024 |
| 9,585,959 B2* | 3/2017 | Tiberg | A61K 9/0024 |
| 9,820,934 B2* | 11/2017 | Nistor | A61K 47/10 |
| 2002/0026027 A1 | 2/2002 | Ansell | |
| 2003/0022242 A1 | 1/2003 | Anderson | |
| 2004/0018241 A1 | 1/2004 | Houze et al. | |
| 2004/0201117 A1 | 10/2004 | Anderson | |
| 2005/0136059 A1 | 6/2005 | Thorpe et al. | |
| 2006/0073203 A1 | 4/2006 | Ljusberg-Wahren et al. | |
| 2007/0080323 A1 | 4/2007 | Joabsson et al. | |
| 2007/0110777 A1 | 5/2007 | Joabsson et al. | |
| 2007/0134336 A1 | 6/2007 | Worle et al. | |
| 2007/0231374 A1 | 10/2007 | Tiberg et al. | |
| 2008/0124394 A1 | 5/2008 | Johnsson et al. | |
| 2008/0146490 A1 | 6/2008 | Joabsson et al. | |
| 2008/0161276 A1 | 7/2008 | Johnsson et al. | |
| 2008/0214995 A1 | 9/2008 | Boyd et al. | |
| 2008/0274176 A1 | 11/2008 | Johnsson et al. | |
| 2009/0069221 A1 | 3/2009 | Joabsson et al. | |
| 2009/0155193 A1 | 6/2009 | Joabsson | |
| 2009/0170782 A1 | 7/2009 | Joabsson et al. | |
| 2010/0178344 A1* | 7/2010 | Lambert | A61K 9/5031 424/486 |
| 2010/0210519 A1 | 8/2010 | Johnsson et al. | |
| 2011/0230569 A1 | 9/2011 | Nistor et al. | |
| 2012/0028890 A1 | 2/2012 | Nistor et al. | |
| 2012/0269772 A1 | 10/2012 | Thuresson et al. | |
| 2014/0162944 A1* | 6/2014 | Tiberg | A61K 9/0019 514/5.3 |
| 2014/0329749 A1* | 11/2014 | Tiberg | A61K 9/0024 514/11.1 |
| 2014/0348903 A1* | 11/2014 | Tiberg | A61K 9/0024 424/450 |
| 2015/0366970 A1* | 12/2015 | Johnsson | A61K 9/127 424/463 |
| 2015/0366973 A1* | 12/2015 | Johnsson | A61K 9/0019 514/11.1 |

FOREIGN PATENT DOCUMENTS

| | | |
|---|---|---|
| WO | 1993/06921 A1 | 4/1993 |
| WO | 1995/34287 A1 | 12/1995 |
| WO | 1997/13528 A1 | 4/1997 |
| WO | 1998/47487 A1 | 10/1998 |
| WO | 2002/02716 A2 | 1/2002 |
| WO | 2002/066014 A2 | 8/2002 |
| WO | 2002/068561 A2 | 9/2002 |
| WO | 2002/068562 A2 | 9/2002 |
| WO | 2003/002136 A1 | 1/2003 |
| WO | 2003/057235 A2 | 7/2003 |
| WO | 2004/087215 A1 | 10/2004 |
| WO | 2005/014162 A1 | 2/2005 |
| WO | 2005/021022 A2 | 3/2005 |
| WO | 2005/046642 A1 | 5/2005 |
| WO | 2005/048952 A2 | 6/2005 |
| WO | 2005/063213 A1 | 7/2005 |
| WO | 2005/070394 A2 | 8/2005 |
| WO | 2005/117830 A1 | 12/2005 |
| WO | 2006/075123 A1 | 7/2006 |
| WO | 2006/075124 A1 | 7/2006 |
| WO | 2006/075125 A1 | 7/2006 |
| WO | 2006/077362 A1 | 7/2006 |
| WO | 2006/131730 A1 | 12/2006 |
| WO | 2007096055 A1 | 8/2007 |
| WO | 2008/152401 A1 | 12/2008 |
| WO | 2009/024795 A1 | 2/2009 |
| WO | 2009/024797 A1 | 2/2009 |
| WO | 2010003939 A1 | 1/2010 |
| WO | 2010/020794 A1 | 2/2010 |
| WO | 2013/083459 A1 | 6/2013 |
| WO | 2013/083460 A1 | 6/2013 |

OTHER PUBLICATIONS

Barauskas et al., Pharmaceutical Nanotechnology, "Interactions of lipid-based liquid crystalline nanoparticles with model and cell membranes", International Journal of Pharmaceutics 391 (2010) pp. 284-291.

R. Berges, "Eligard: Pharmacokinetics, Effect on Testosterone and PSA Levels and Tolerability," European Urology Supplements, 2005, vol. 4, pp. 20-25.

P. Chanson et al., "Comparison of octreotide acetate LAR and lanreptide SR in patients with acromegaly," Clin. Endocrinology, 2001, vol. 54, No. 1, pp. 11-13, (Abstract only).

Comets et al., "Non parametric analysis of the absorption profile of octreotide in rabbits from long-acting release formulation OncoLAR," J. Controlled Release 59:197-205 (1999).

B. L. Erstad, "Octreotide for acute variceal bleeding," Ann. Pharmacother., 2001, vol. 35, No. 5, pp. 618-626. (Abstract only).

Evaluate™: "Camurus Announces Positive Phase 1 Results With it's New Long-Acting Octreotide Product CAM2029," obtained from http://www.evaluategroup.com on Dec. 27, 2014, pp. 1-2, dated Apr. 24, 2007.

FDA's 510(k) Summary of Camurus AB, episil® K101769 (2011).

A. K. Flogstad et al., "Sandostatin LAR in acromegalic patients: long term treatment," J. Clinical Endocrinology & Metabolism, 1997, vol. 82, No. 1, pp. 23-28.

P. R. Gibson & J. G. Muir, "Reinforcing the mucus: a new therapeutic approach for ulcerative colitis," Gut, 2005, vol. 54, pp. 900-903.

L. M. Grant & F. Tibert, "Normal and Lateral Forces between Lipid Covered Solids in Solution: Correlation with Layer Packing and Structure," Biophysical Journal, 2002, vol. 82, pp. 1373-1385.

B.A. Hills, "Surface-active phospholipid: a Pandora's box of clinical applications. Part II. Barrier and lubricating properties," Internal Medicine Journal, 2002, vol. 32, pp. 242-251.

G. G. Holz et al., "Glucagon-Like Peptide-1 Synthetic Analogs: New Therapeutic Agents for Use in the Treatment of Diabetes Mellitus," Current Medicinal Chemistry (2003), vol. 10, pp. 2471-2483.

H. Hui et al., "Structure and function studies of glucagon-like peptide-1 (GLP-1): the designing of a novel pharmacological agent for the treatment of diabetes," Diabetes Metabolism Research and Reviews, (2005), vol. 21, pp. 313-331.

Information on Goserelin Subcutaneous, Monograph—Goserelin Acetate, pp. 1-7, print out form www.medscape.com (2005).

Invitrogen, "Pluronic F-127", Molecular Probes Invitrogen Detection Technologies, pp. 1-2, 2008.

Johnsson et al., "Physicochemical and Drug Delivery Aspects of Lipid-Based Liquid Crystalline Nanoparticles: A Case Study of Intravenously Administered Propofol", Journal of Nanoscience and Nanotechnology, vol. 6, No. 9/10, pp. 3017-3024, 2006.

Kamo et al.: "Nonlamellar Liquid Crystalline Phases and Their Particle Formation in the Egg Yolk Phosphatidylcholine/Diolein System," Langmuir, vol. 19, pp. 9191-9195, Published on Web Oct. 1, 2003.

Kesisoglou et al.: "Liposomal Formuations of Inflammatory Bowel Disease Drugs: Local Versus Systemic Drug Delivery in a Rat Model," Pharmaceutical Research, vol. 22, No. 8, pp. 1320-1329, Aug. 2005.

J. G. M. Klijn et al., "Combined tamoxifen and luteinizing hormone-releasing hormone (LHRH) agonist versus LHRH agonist alone in premenopausal advanced breast cancer: A meta-analysis of four randomized trials," Journal of Clinical Oncology, 2001, vol. 19, No. 2, pp. 343-353 (Abstract only).

L. M. Knudsen et al., "Potent Derivatives of Glucagon-like Peptide-1 with Pharmacokinetic Properties Suitable for Once Daily Administration," J. Med. Chem. (2000) vol. 43, pp. 1664-1669.

(56) References Cited

OTHER PUBLICATIONS

L. M. Knudsen, "Glucagon-like Peptide-1: The Basis of a New Class of Treatment for Type 2 Diabetes," J. Med. Chem. (2004), vol. 47, pp. 4128-4134.

I. Lancranjan et al., "Sandostatin LAR: Pharmacokinetics. Pharmacodynamics, Efficacy and Tolerability in Acromegalic Patients," Metabolism, 1995, vol. 44, No. 1, pp. 18-26.

"Leutinizing Hormone Releasing Hormone (LHRH) Agonists: Goserelin (Zoladex) vs. Leuprolide (Lupron) for Prostate Cancer," DoD Pharmacoeconomic Center Update, Newsletter, Dec. 2000, vol. 1, No. 1, print out from http://www.pec.ha.osd.mil.com, pp. 1-3.

Loughrey et al., "Development of a Sensitive Sandwich ELISA For Detecting Full Length Biologically Active TH0318, a GLP-1 Analogue," presented at the 2005 AAPS Annual Meeting and Exposition, Abstract No. W5009 (2005).

Martel et al., "Enzyme Linked Immunosorbent Assay (EUSA) Method for the Determination of TH0318, a New GLP-1 Analogue in Development for Diabetes," presented at the 2005 MPS Annual Meeting and Exposition, Abstract No. W5008 (2005).

MSDS for Ethylene Glycol and Abbreviations used in Toxicity data (2009).

Novartis Pharmaceuticals Corporation, "Sansdostatin LAR Depot (octreotide acetate for injectable suspension)", pp. 1-19 (2005).

PDR Information on Eligard 30 mg (Sanofi-Synthelabo), print out from www.Drugs.com, pp. 1-14.

Pharmaceutical Information on Lupron Depot, print out from www. rxmed.com, pp. 1-8 (2004).

Product Specification of Leuprolide by GL Biochem, print out from http://www.glschina.com (2005).

Published Data Provided by Sandostatin LAR "The Latest Research and Treatment Information for Pituitary Disorders" from http://www.sandostatin.com/published data/index.html (2005).

O. Sartor "Eligard: Leuprolide Acetate in a Novel Sustained-Release Delivery System," Urology, 2003, vol. 61, (Supplement 2A), pp. 25-31.

K. J. Schuh et al., "Onset, magnitude and duration of opioid blockade produced by buprenorphine and naltrexone in humans," Psychopharmacology, (Berl), Jul. 1999, vol. 145, No. 2, pp. 162-174 (Abstract only).

J. C. Shah et al., "Cubic phase gels as drug delivery systems," Advanced Drug Delivery Reviews, 2001, vol. 47, pp. 229-250.

W. Stremmel et al., "Retarded release phosphatidylcholine benefits patients with chronic active ulcerative colitis," Gut, 2005, vol. 54, pp. 966-971.

A Sturm & A. U. Dignass, "Modulation of gastrointestinal wound repair and inflammation by phospholipids," Biochimica et Biophysica Acta, 2002, vol. 1582, pp. 282-288.

Svanberg et al., "A New Preventive Strategy Using a Bioadhesive Oromucosal Lipid Solution and Oral Cryotherapy to Protect The Oral Cavity—and Reduce The Need for Total Parenteral Nutrition (Tpn) for Patients Undergoing Autologous Stemcell Transplantation," Support Care Cancer 18 (Suppl 3):S114-S115, at Abstract 08-076 (2010) (attached hereto as Annex 5 to Evidentiary Declaration Under 37 C.F.R. § 1.132 of Fredrik Tiberg).

About Sandostatin: Proven Control of GH, 1GF-1 and Gastrointestinal Hormone, from www.sandostatin.com/about.sandostatin/index.html and linked documents (2005).

Office Action in U.S. Appl. No. 12/664,835 dated Jan. 2, 2015.

International Search Report in PCT Application No. PCT/EP2013/060739 dated Nov. 28, 2013.

International Preliminary Report on Patentability in PCT Application No. PCT/EP2013/060739 dated Nov. 25, 2014.

Tiberg et al., "Drug delivery applications of non-lamellar liquid crystalline phases and nanoparticles", J. Drug Del. Sci. Tech., 21 (1)pp. 101-109, 2011.

Tiberg et al., "Treatment of oral mucositis pain by a bioadhesive barrier forming lipid solution," Camurus (attached hereto as Annex 3 to Evidentiary Declaration Under 37 C.F.R. § 1.132 of Fredrik Tiberg).

Tiberg et al., "Treatment of Oral Mucositis Pain by a Bioadhesive Barrier Forming Lipid Solution," Support Care Center 17(7):918 (2009) (attached hereto as Annex 4 to Evidentiary Declaration Under 37 C.F.R. § 1.132 of Fredrik Tiberg).

Tiberg et al.: Camurus Received Positive Opinion for Orphan Drug Designation for CAM2029, Camurus AB, pp. 1-2, May 26, 2009.

Tiberg et al.: "Lipid Liquid Crystals for Prenteral Sustained-Release Applications: Combining Ease of Use and Manufacturing with Consistent Drug Release Control," obtained from www.ondrugdelivery.com on Dec. 27, 2014; pp. 9-13, 2010.

Tiberg: "Camurus Announces Positive Phase 1 Results with it New Long-Acting Octreotide Products CAM2029," Camurus AB; pp. 1-2, Apr. 24, 2007.

Treating Acromegaly, from http://www.sandostatin.com/lreating acromegaly/index.html and linked documents (2005).

Welin et al., "High-dose treatment with a long-acting somatostatin analogue in patients with advanced midgut carcinoid tumours," 2004, Society of the European Journal of Endocrinology, vol. 151, pp. 107-112.

E. Woltering et al., "Octreotide acetate (LAR) dose effect on plasma octreotide levels: Impact on neuroendocrine tumor Management," F. Clin Oncology, 2005 ASCO Annual Meeting Proceedings, vol. 23, No. 16S, pp. 3177 (Abstract only) (2005).

International Search Report in PCT Application No. PCT/EP2012/059917 dated Nov. 29, 2012.

International Preliminary Report on Patentability in PCT Application No. PCT/EP2012/059917 dated Nov. 26, 2013 (and Written Opinion).

International Search Report of PCT/GB2005/004745 dated May 8, 2006.

International Preliminary Report on Patentability of PCT/GB2005/004745 dated Jul. 20, 2007.

Written Opinion of PCT/GB2005/004745 dated May 8, 2006.

International Search Report of PCT/GB2005/04748 dated Mar. 23, 2006.

International Preliminary Reporton Patentability of PCT/GB2005/04748 dated Mar. 12, 2007.

Written Opinion of PCT/GB2005/04748 dated Mar. 23, 2006.

International Search Report of PCT/GB2005/04752 dated Mar. 17, 2006.

International Preliminary Reporton Patentability of PCT/GB2005/04752 dated Mar. 12, 2007.

Written Opinion of PCT/GB2005/04752 dated Mar. 17, 2006.

International Search Report of PCT/GB2005/004746 dated Mar. 16, 2006.

International Preliminary Report on Patentability and Written Opinion of PCT/GB2005/004746 dated Jul. 17, 2007.

International Search Report of PCT/GB2006/002079 dated Aug. 25, 2006.

International Preliminary Report on Patentability and Written Opinion of PCT/GB2006/002079 dated Dec. 6, 2007.

International Search Report of PCT/GB2008/002035 dated Oct. 6, 2008.

International Preliminary Report on Patentability of PCT/GB2008/002035 dated Dec. 17, 2009.

Written Opinion of PCT/GB2008/002035 dated Oct. 6, 2008.

International Search Report of PCT/GB2008/002857 dated Jan. 28, 2009.

International Preliminary Report on Patentability and Written Opinion of PCT/GB2008/002857 dated Feb. 24, 2010.

International Search Report of PCT/GB2009/002054 dated Nov. 30, 2009.

International Preliminary Report on Patentability and Written Opinion of PCT/GB2009/002054 dated Feb. 22, 2011.

Office Action in U.S. Appl. No. 11/795,242 dated Dec. 23, 2011.
Office Action in U.S. Appl. No. 11/795,242 dated Jan. 10, 2013.
Office Action in U.S. Appl. No. 11/795,243 dated May 12, 2011.
Office Action in U.S. Appl. No. 11/795,243 dated Mar. 22, 2012.
Office Action in U.S. Appl. No. 11/795,243 dated Apr. 23, 2014.
Office Action in U.S. Appl. No. 11/795,249 dated Oct. 25, 2010.
Office Action in U.S. Appl. No. 11/795,249 dated Jul. 19, 2011.
Office Action in U.S. Appl. No. 11/795,249 dated Dec. 4, 2013.
Office Action in U.S. Appl. No. 11/795,250 dated Jun. 24, 2010.

(56) References Cited

OTHER PUBLICATIONS

Office Action in U.S. Appl. No. 11/795,250 dated Mar. 18, 2011.
Office Action in U.S. Appl. No. 11/795,250 dated Dec. 21, 2012.
Office Action in U.S. Appl. No. 11/795,250 dated Dec. 4, 2013.
Office Action in U.S. Appl. No. 11/877,935 dated Dec. 21, 2010.
Office Action in U.S. Appl. No. 11/908,740 dated Feb. 14, 2012.
Office Action in U.S. Appl. No. 12/664,835 dated Feb. 12, 2013.
Office Action in U.S. Appl. No. 12/664,835 dated Oct. 25, 2013.
Office Action in U.S. Appl. No. 13/060,121 dated Jul. 8, 2013.
"Acromegaly" from www.niddk.nil.gov/health/endo/pubs/acro/acro.htm; NIH Publication No. 02-3924, Jun. 2002.
American Peptide Company, Product Details "Somatostatin and analogs," from www.americanpeptide.com, 2003.
Chang, J., "Use of GnRH agonists in the treatment of hyperandrogenism and hirsutism," print out from http://patients.uptodate.com, Jul. 7, 2004.
F. Dall'Antonia, "Structure determination of organo-silicon compounds.", pp. 6 to 8 from http://shelx.uni-ac.gwdg.de/-fabio/endwkcon.htm, 2006.
Definition of analog from http://cancerweb.ncl.ac.uk!omd/about.html, pp. 1-5. Accessed Jul. 7, 2005.
Indications and Usage of Eligard, pp. 1-5, print out from http:ffwww.rxlist.com, Jul. 2003.
Information on Leuprolide (3 Month) Intramuscular, Monograph-Leuprolide Acetate, pp. 1-20, print out from www.medscape .com, 2005.
Information on Leuprolide Intramuscular, Monograph- Leuprolide Acetate, pp. 1-20, print out for www.medscape.com, 2005.
Martel et al., "Enzyme Linked Immunosorbent Assay (EUSA) Method for the Determination of TH0318, a New GLP-1 Analogue in Development for Diabetes," Poster, presented at the 2005 MPS Annual Meeting and Exposition.
Product Information on Zoladex Goserelin Acetate Implant (Equivalent to 10.8 mg goserelin), Astrazeneca, Rev. 10, 2001.
"Setting new standards of care," Mixing and Administration instructions for Sandostatin LAR, Novartis, 2003.
Wermuth, Pure and Appl. Chem, 1998, 70, 1129-1143.
E. A. Woltering, "A discussion on the utility of various routes of administration of octreotide acetate," from http://www.carcinoid.org/medpro/docs/WoltPump2005.htm, 2005.

\* cited by examiner

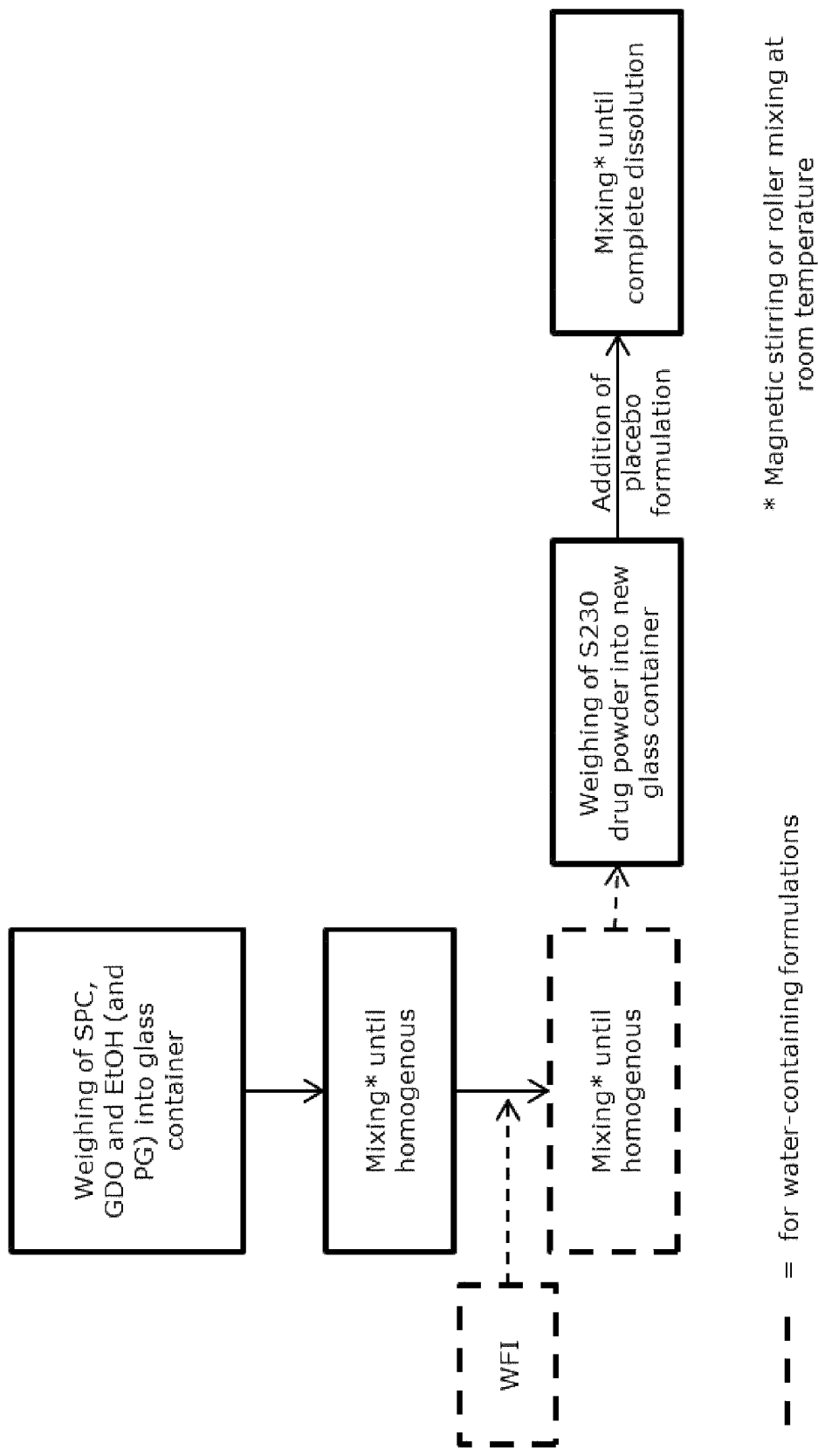
Figure 1. Flow chart describing the preparation of lipid/S230 (pasireotide) samples for solubility screening.

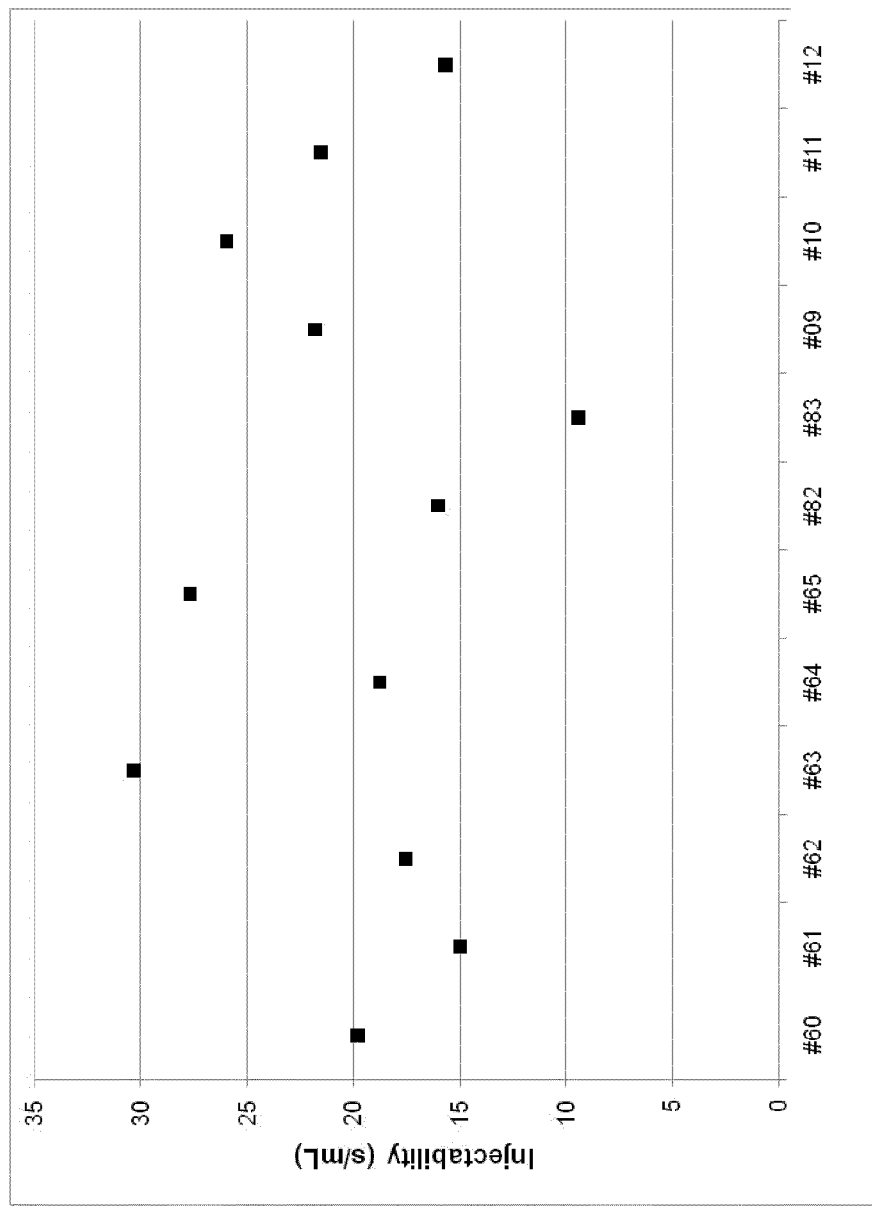
Figure 2. Injectability (seconds/mL) measured at 20N constant force as a function of formulation composition (see Table 3).

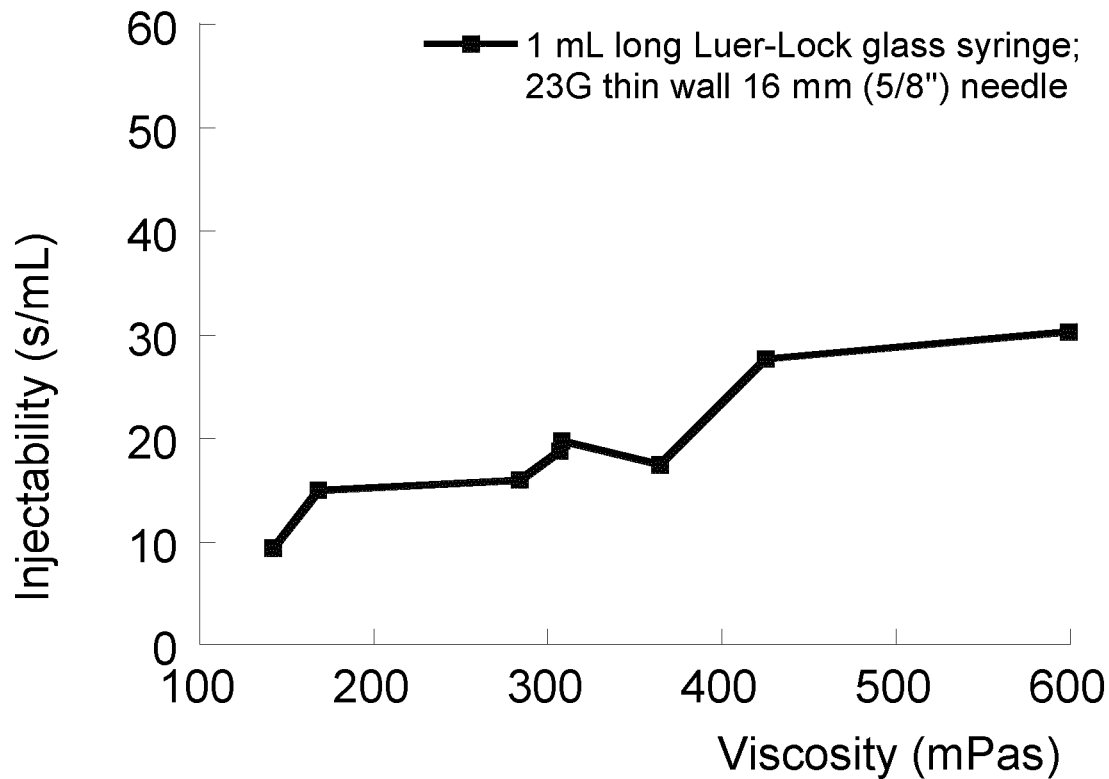
Figure 3. Injectability (seconds per mL), measured at 20N constant force, as a function of formulation viscosity.
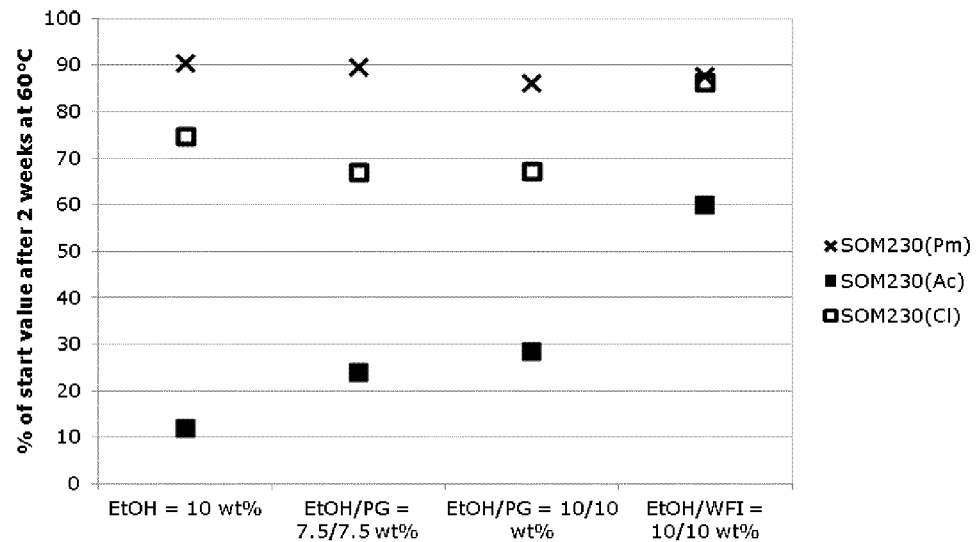
Figure 4. Comparison of stability data on lipid/pasireotide formulations for various salts, differentiated by their respective solvent composition

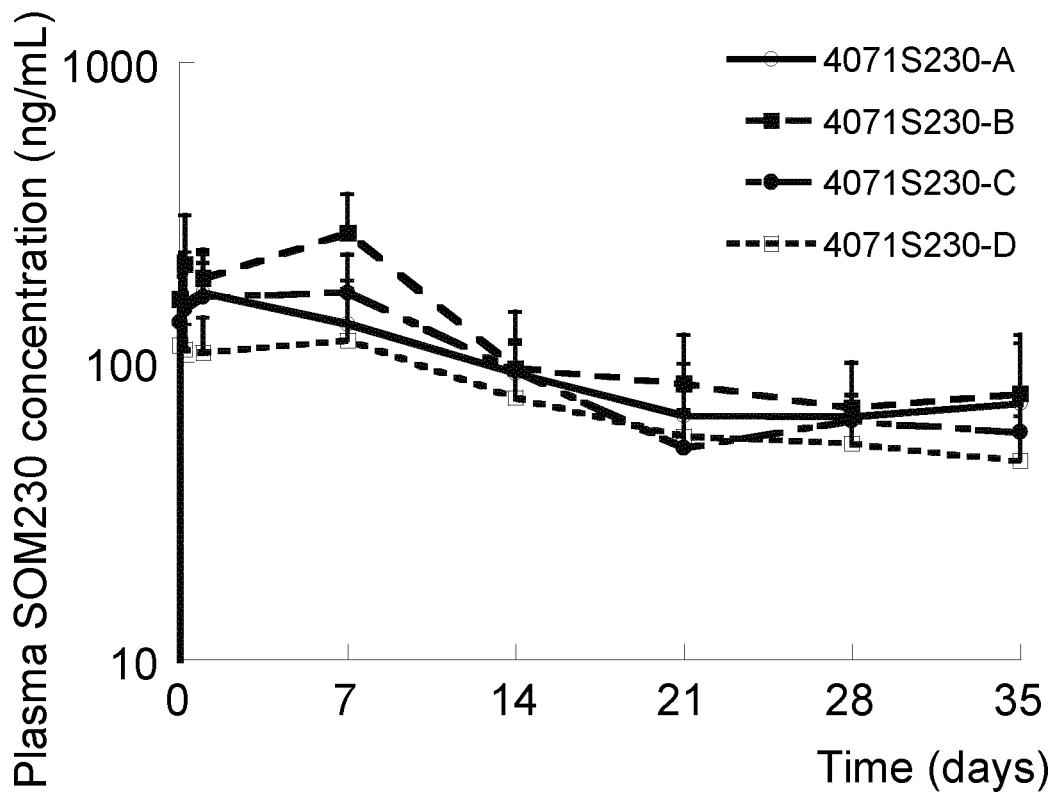
Figure 5. Mean plasma concentrations (n = 6) of SOM230 (pasireotide pamoate) after s.c. injection in rats.
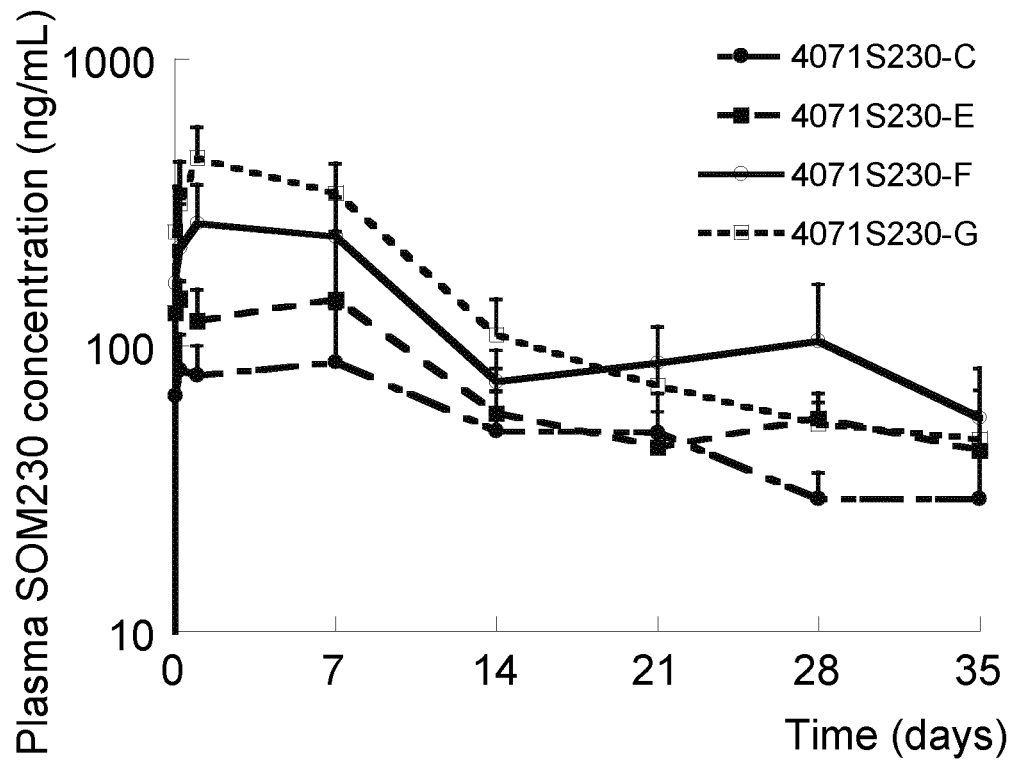
Figure 6. Mean plasma concentrations (n = 6) of SOM230 (pasireotide pamoate) after s.c. injection in rats.

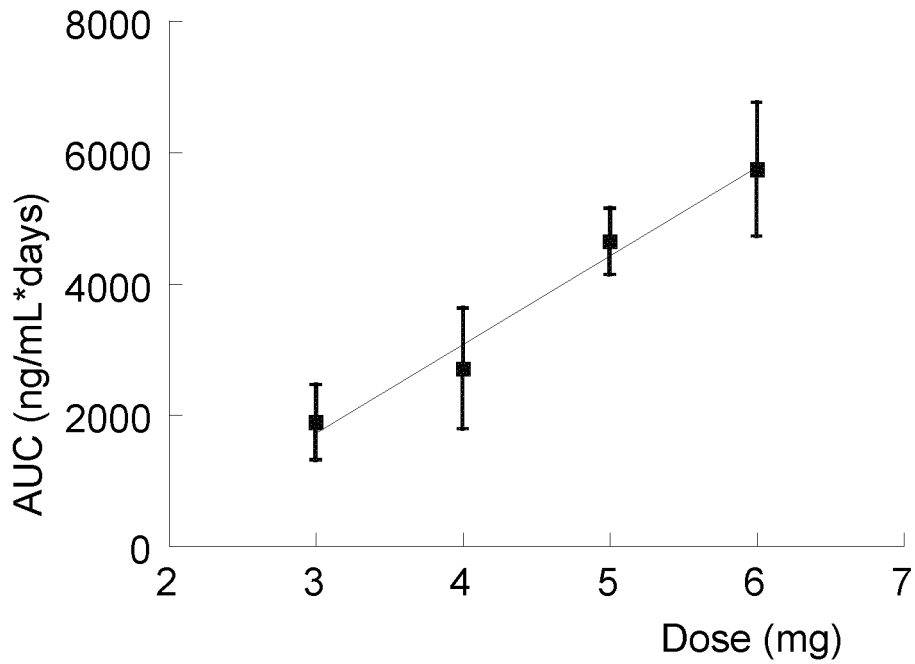
Figure 7. Dose linearity with respect to exposure (AUC) in study PK-12-438. Error bars represent standard deviation.
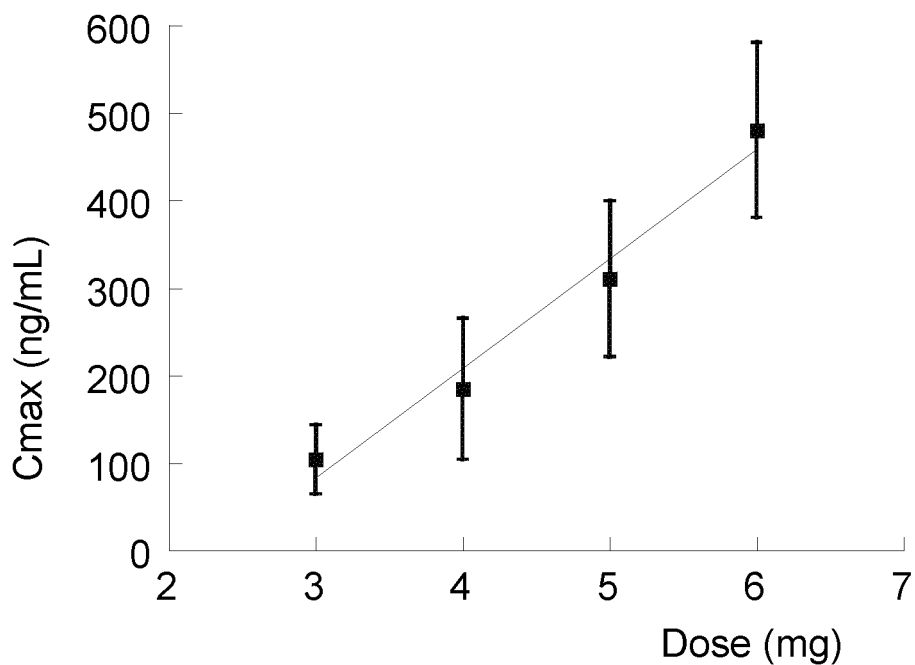
Figure 8. Dose linearity with respect to Cmax in study PK-12-438. Error bars represent standard deviation.

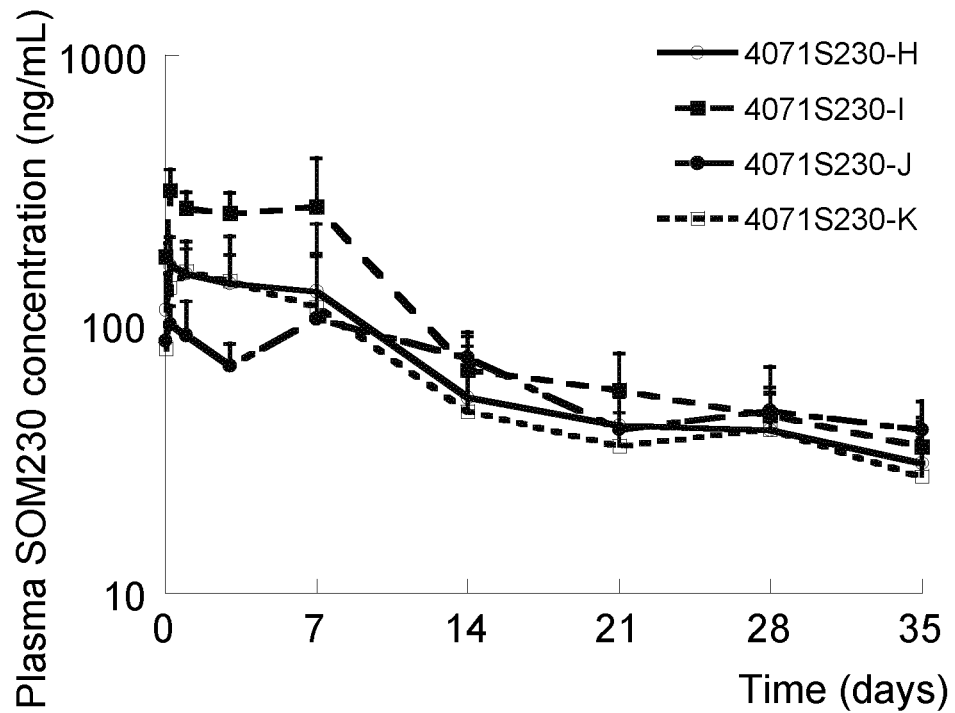
Figure 9. Mean plasma concentrations (n = 6) of SOM230 (pasireotide pamoate) after s.c. injection in rats.
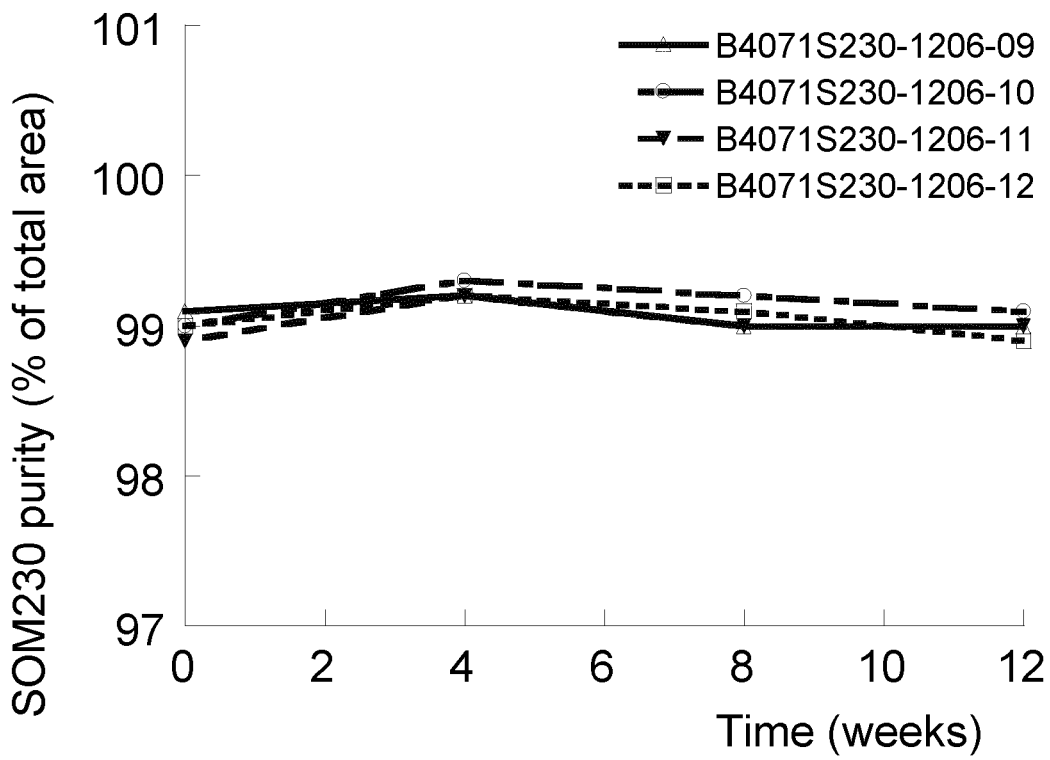
Figure 10. The SOM230 purity after storage at 5°C. The figure legend refers to the respective batch number as indicated in Table 19.

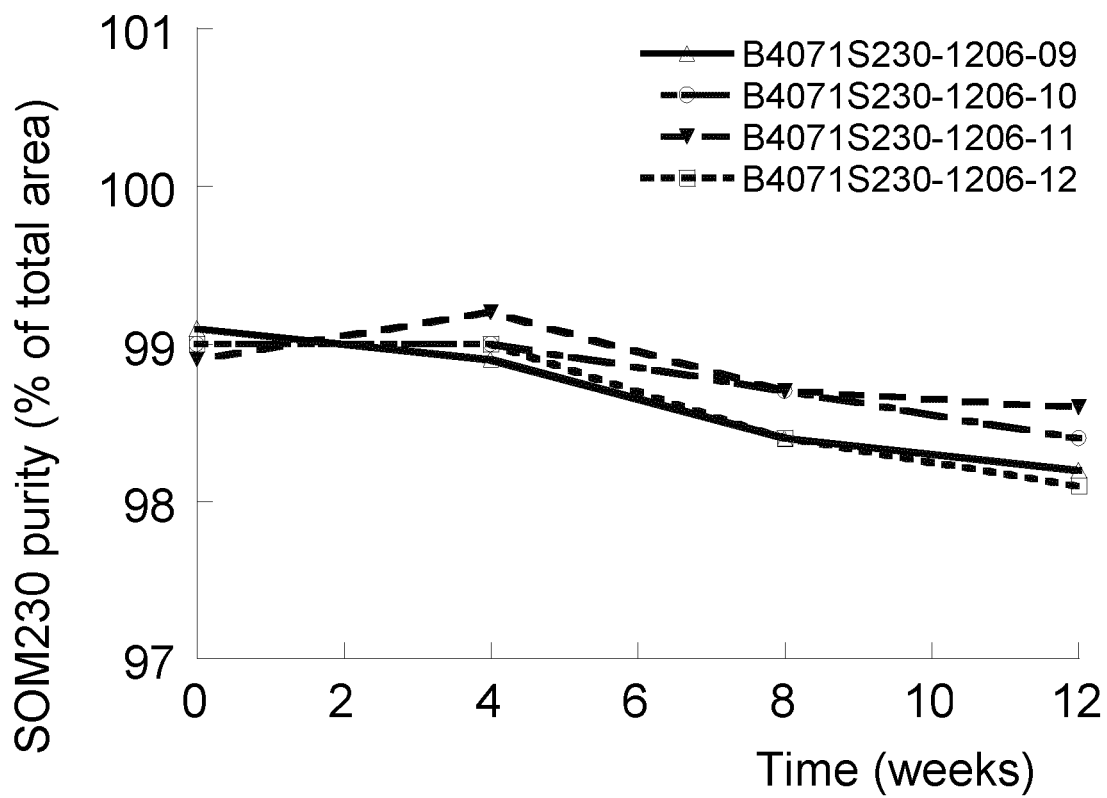
Figure 11. The SOM230 purity after storage at 25°C/60% RH. The figure legend refers to the respective batch number as indicated in Table 19.

```
                      SEQUENCE LISTING

<160> NUMBER OF SEQ ID NOS: 2

<210> SEQ ID NO 1
<211> LENGTH: 14
<212> TYPE: PRT
<213> ORGANISM: Homo sapiens

<400> SEQUENCE: 1

Ala Gly Cys Lys Asn Phe Phe Trp Lys Thr Phe Thr Ser Cys
1               5                   10

<210> SEQ ID NO 2
<211> LENGTH: 4
<212> TYPE: PRT
<213> ORGANISM: Homo sapiens

<400> SEQUENCE: 2

Phe Trp Lys Thr
1
```

SOMATOSTATIN RECEPTOR AGONIST FORMULATIONS

FIELD OF THE INVENTION

The present invention relates to formulation precursors (pre-formulations) for the in situ generation of compositions for the controlled release of peptide active agents, and methods of treatment with such formulations. In particular, the invention relates to high-loading pre-formulations of amphiphilic components and at least one peptide active agent comprising pasireotide for parenteral application, which undergo phase transition upon exposure to aqueous fluids, such as body fluids, thereby forming a controlled release composition.

BACKGROUND TO THE INVENTION

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable or necessary, since self-administration may be difficult and thus cause inconvenience and/or poor compliance. In such cases it would be advantageous for a single administration to provide active agent at a therapeutic level over the whole period during which activity is needed.

There is an enormous potential in the use of peptides (including proteins) for treating various disease states, as well as in prophylaxis and in improving general health and well-being of subjects. However, the performance of administered peptide agents is generally limited due to poor bioavailability, which in turn is caused by the rapid degradation of peptides and proteins in biological fluids. This increases the dose which must be administered and in many cases restricts the effective routes of administration. These effects are further exaggerated by the often limited permeability of peptides and proteins across biological membranes.

Peptides and proteins that are administered to the mammalian body (e.g. orally, intramuscularly etc.) are subject to degradation by various proteolytic enzymes and systems present throughout the body. Well known sites of peptidase activity include the stomach (e.g. pepsin), and the intestinal tract (e.g. trypsin, chymotrypsin, and others) but other peptidases (e.g. aminopeptidases, carboxypeptidases, etc.) are found throughout the body. Upon oral administration, gastric and intestinal degradation reduces the amount of peptide or protein which potentially could be absorbed through the intestinal surface lining and thereby decreases their bioavailability. Similarly, free peptides and proteins in the mammalian blood stream are also subject to enzymatic degradation (e.g. by plasma proteases etc.).

Some patients undergoing treatment will typically require a therapeutic dose to be maintained for a considerable period and/or ongoing treatment for many months or years. Thus a depot system allowing loading and controlled release of a larger dose over a longer period would offer a considerable advantage over conventional delivery systems.

Peptides may be delivered by systems such as the Alkermes Medisorb® delivery system consisting of microspheres of biodegradable polymers. Such polymer microsphere formulations must generally be administered by means of a sizable needle, typically of 20-gauge or wider. This is necessary as a result of the nature of the polymeric dosing systems used, which are typically polymer suspensions.

Evidently, it would be an advantage to provide a system of low viscosity, such as a homogeneous solution, dispersion of fine particles, or $L_2$ phase, which could be administered easily through a narrow needle, thus decreasing the discomfort of the patient during the procedure. This ease of administration is particularly significant where patients will be on a self-administration regime and may already be self-administering several times each day. Providing a sustained formulation with a duration of a few days, but which is sufficiently complex to administer that it requires treatment by a healthcare professional will not be an advantage to all patients over twice-daily or daily self-administration, and is likely to be more costly. Providing a formulation which gives sufficiently long duration to justify a visit to a health professional for administration and/or a preparation which can be self-administered, and reducing preparation time of health-care professionals or patients prior to the actual administration are all important issues.

The poly-lactate, poly-glycolate and poly-lactate-co-glycolate polymers typically used for degrading slow-release formulations are also the cause of some irritation in at least some patients. In particular, these polymers typically contain a certain proportion of acidic impurities such as lactic and glycolic acid, which will irritate the injection site on administration. When the polymer then breaks down, lactic acid and glycolic acid are the degradation products so that further irritation is caused. As a result of the combined effects of wide-needle administration and irritant contents, discomfort at the site of administration and the formation of connective scar tissue are greater than desirable.

From a drug delivery point of view, polymer depot compositions generally have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, and then drop back through the bottom of the functional window during the lag period before reaching a sustained functional concentration for a period of time. Evidently, from a functional and toxicological point of view this burst/lag release profile is undesirable and could be dangerous. It may also limit the equilibrium concentration which can be provided due to the danger of adverse effects at the "peak" point. The presence of a lag phase may furthermore require supplementary dosing with repeat injections during the start-up period of depot treatment in order to maintain a therapeutic dose while the concentrations of active provided from the depot are sub-functional. For certain polypeptides in particular, it would be advantageous to minimise the immediate "burst" effect upon administration of a composition in order to avoid side effects such as hypoglycaemia.

One class of peptide hormones which benefits particularly from a very "low burst", stable in vivo concentration are Somatostatin analogues such as Pasireotide (SOM230). In vivo testing suggests that these peptides are particularly beneficial when maintained at a steady plasma concentration and as a regulatory hormone, Pasireotide is particularly likely to benefit from a stable plasma level. This not only suggests that a depot composition would be an advantage to avoid "spikes" in concentration upon administration and/or repeated daily dosing, but furthermore that such a depot composition should have as flat a release profile as possible during the therapeutic period.

Controlled-release formulations are typically generated from bio-compatible polymers in the form of, for example, implants or injectable beads. The current leading formulation of Pasireotide, for example (Pasireotide LAR) comprises microparticles of poly (D,L-lactide-co-glycolide). Polymer microsphere formulations must generally be administered by means of a sizable needle, typically of 20-gauge or wider. This is necessary as a result of the nature of the polymeric dosing systems used, which are typically polymer suspensions. It would be an advantage to provide a system of low viscosity, such as a homogeneous solution, dispersion of fine particles, or $L_2$ phase, which could be administered easily through a narrow needle, thus decreasing the discomfort of the patient during the procedure. Ease of administration is particularly significant when patients will be self-administering but also reduces the burden on healthcare professionals when they are conducting the administration.

The manufacture of PLGA microbeads and suspensions is additionally a considerable difficulty with certain existing depot systems. In particular, since the beads are particulate they cannot generally be sterile-filtered and furthermore, since the PLGA copolymer melts at elevated temperature, they cannot be heat-treated for sterility. As a result, the complex manufacturing process must be conducted aseptically.

Further issues with biodegradable polymer microspheres include complex reconstitution prior to injection and limited storage stability, due both to aggregation and degradation of the delivery system and/or active.

A lipid-based, slow-release composition has been described for certain peptides. For example, WO2006/131730 discloses a lipid depot system for GLP-1 and analogues thereof. This is a highly effective formulation, but the concentration of active agent which can be included in the formulation is limited by its solubility. Evidently, a higher concentration of active agent allows for the possibility of longer duration depot products, products maintaining a higher systemic concentration, and products having a smaller injection volume, all of which factors are of considerable advantage under appropriate circumstances. It would thus be of considerable value to establish a way by which higher concentrations of active agents could be included in a lipid-based depot formulation and to identify combinations of active agent and delivery system which are particularly effective from the point of view of loading, stability, manufacturing and/or controlled release.

The present inventors have now established that by providing a pre-formulation comprising at least one neutral diacyl glycerol, at least one phosphatidyl choline, at least one biocompatible organic mono-alcoholic solvent, at least one polar solvent, at least one peptide active agent comprising pasireotide (SOM230) and optionally at least one anti-oxidant in a low viscosity phase, such as molecular solution or $L_2$ (reversed micellar) phase, a pre-formulation may be generated addressing many of the shortfalls of known depot formulations, and which may be applied to provide a controlled release of the pasireotide active agent. By use of specific components in carefully selected ratios, and in particular with a mixture of pasireotide, an alcohol and a polar solvent, a depot formulation can be generated having a combination of properties exceeding the performance even of previous lipid controlled-release compositions and providing an advantage over known compositions such as pasireotide LAR.

In particular, the pre-formulation shows a highly advantageous release profile, is easy to manufacture, may be sterile-filtered, has low viscosity (allowing easy and less painful administration typically through a narrow needle), allows a high level of bioactive agent to be incorporated (thus potentially allowing a smaller amount of composition and/or active agent to be used), requires shallow injection and/or forms a desired non-lamellar depot composition in vivo having a "non-burst" release profile. The compositions are also formed from materials that are non-toxic, biotolerable and biodegradable, which can be administered by i.m., or s.c. injection and are suitable for self-administration. The pre-formulation may additionally have a very low level of irritation on injection and in preferred cases causes no irritation at the injection site (including transient irritation).

Certain of the formulations of the present invention generate a non-lamellar liquid crystalline phase following administration. The use of non-lamellar phase structures (such as non-lamellar liquid crystalline phases) in the delivery of bioactive agents is now relatively well established. A most effective lipid depot system is described in WO2005/117830, and a highly preferred lipid depot is described in that document. However, there remains scope for achieving depot formulations having improved performance in several respects and in particular, surprising improvements can be achieved by careful selection and optimisation of the range of components and proportions disclosed in previous work.

Advantages of the compositions of the present invention over polymer formulations, such as PLGA microspheres, include the ease of manufacture (including sterilization), handling and use properties combined with low initial release ("non-burst profile") of active agent. This may be defined such that the area under a plasma concentration against time the curve during the first 24 hours of a one-month dosing period is less than 20% of the area under the curve for the entire curve (measured or extrapolated from time 0 to infinity or from time 0 to the last sampling time point), more preferably less than 15% and most preferable less than 10%. Furthermore, it may be defined such that the maximum plasma concentration of active agent in vivo following injection of the pre-formulation (Cmax) is no more than 10 times, preferably no more than 8 times and most preferably no more than 5 times the average plasma concentration during the therapeutic period (Cave) (i.e. Cmax/Cave ≤10, preferably ≤8, more preferably ≤5).

SUMMARY OF THE INVENTION

The present invention provides a pharmaceutical formulation comprising an appropriate combination of lipid excipients, organic alcoholic solvent, polar solvent, peptide active agent comprising pasireotide and certain optional components, that can be used as a depot-precursor formulation (referred to herein for brevity as a pre-formulation) to address one or more of the needs described above. The inventors have established that by optimising these components, depot compositions of pasireotide and corresponding precursor formulations with a highly advantageous combination of properties can be generated.

In a first aspect, the invention therefore provides a pre-formulation comprising a low viscosity mixture of:
- a. 20-50 wt. % of at least one diacyl glycerol;
- b. 20-54 wt. % of at least one phosphatidyl choline (PC);
- c. 5-15 wt. % of at least one biocompatible, organic mono-alcoholic solvent;
- d. 1 to 20 wt. % polar solvent
- e. 5 to 150 mg/ml of at least one peptide somatostatin receptor agonist comprising pasireotide (calculated as the free base);
- f. optionally at least one antioxidant;

wherein the ratio of components a:b is in the range 40:60 to 54:46;
wherein the pre-formulation forms, or is capable of forming, at least one liquid crystalline phase structure upon contact with excess aqueous fluid.

Such compositions will preferably comprise glycerol dioleate (GDO), soy PC and/or high purity PC, (such as PC with at least 95% PC head groups and at least 95% C16 to C20 acyl groups having 0 to 3 unsaturations), ethanol, water/propylene glycol and/or EDTA as components a), b), c), d) and f) respectively. Component e) comprises or consists of pasireotide or a salt thereof preferably wherein said salt is a biotolerable salt, such as one selected from the chloride, acetate, pamoate and tartrate salts, most preferably the pamoate salt, as described herein.

In a second embodiment, the invention correspondingly provides a process for the formation of a pre-formulation suitable for the administration of a peptide somatostatin receptor agonist comprising pasireotide to a (preferably mammalian) subject, said process comprising forming a low viscosity mixture of:
- a) 20-50 wt. % of at least one diacyl glycerol;
- b) 20-54 wt. % of at least one phosphatidyl choline (PC);
- c) 5-215 wt. % of at least one biocompatible, organic mono-alcoholic solvent;
- d) 1 to 20 wt. % polar solvent
- e) 5 to 150 mg/ml of at least one peptide somatostatin receptor agonist comprising pasireotide (calculated as the free base);
- f) optionally at least one antioxidant;

wherein the ratio of components a:b is in the range 40:60 to 54:46;
and dissolving or dispersing the at least one peptide somatostatin receptor agonist (preferably a somatostatin analogue) in the low viscosity mixture, or in at least one of components a), b), c), d) and optionally f) prior to forming the low viscosity mixture. Such a pre-formulation will typically be one as described herein.

The preformulations are highly useful for the controlled and sustained release of peptide active, especially those requiring or benefiting from a very flat release profile and/or minimal "burst" upon administration. In a corresponding embodiment, the invention therefore provides for the use of a low viscosity mixture of:
- a) 20-50 wt. % of at least one diacyl glycerol;
- b) 20-54 wt. % of at least one phosphatidyl choline (PC);
- c) 5-20 wt. % of at least one biocompatible, organic mono-alcoholic solvent;
- d) 1 to 20 wt. % polar solvent
- e) 5 to 150 mg/ml of at least one peptide somatostatin receptor agonist comprising pasireotide (calculated as free base);
- f) optionally at least one antioxidant;

wherein the ratio of components a:b is in the range 40:60 to 54:46;
in the manufacture of a pre-formulation for use in the sustained administration of said peptide somatostatin receptor agonist. Such a low viscosity mixture will preferably be one described herein.

The peptide somatostatin receptor agonists in the formulations of the present invention are preferably pharmaceutically active. That is to say that they provide a therapeutic, palliative and/or prophylactic effect when administered to a suitable subject (typically being one in need of such an effect). In a further embodiment, the invention therefore provides a method for the treatment of a human or non-human mammalian subject comprising administering to said subject a pre-formulation as described herein.

Such a method may be for the treatment of a human or non-human mammalian subject in need thereof to combat, (e.g. cure, treat, improve, prevent, palliate and/or ameliorate the symptoms of) at least one condition selected from Cushing's disease, acromegaly, type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, e.g. morbid obesity or hypothalamic or hyperinsulinemic obesity, enterocutaneous and pancreaticocutaneous fistula, irritable bowel syndrome, inflammatory diseases, e.g. Grave's Disease, inflammatory bowel disease, psoriasis or rheumatoid arthritis, polycystic kidney disease, dumping syndrome, watery diarrhea syndrome, AIDS-related diarrhea, chemotherapy-induced diarrhea, acute or chronic pancreatitis and gastrointestinal hormone secreting tumors (e.g. GEP tumors, for example vipomas, glucagonomas, insulinomas, carcinoids and the like), lymphocyte malignancies, e.g. lymphomas or leukemias, hepatocellular carcinoma as well as gastrointestinal bleeding, e.g variceal oesophagial bleeding. The preformulations as described herein for use in such methods form a further aspect of the invention.

Correspondingly, in a further aspect, the present invention provides the use of a low viscosity mixture of:
- a) 20-50 wt. % of at least one diacyl glycerol;
- b) 20-54 wt. % of at least one phosphatidyl choline (PC);
- c) 5-15 wt. % of at least one biocompatible, organic mono-alcoholic solvent;
- d) 1 to 20 wt. % polar solvent
- e) 5 to 150 mg/ml of at least one peptide somatostatin receptor agonist comprising pasireotide (calculated as free base);
- f) optionally at least one antioxidant;

wherein the ratio of components a:b is in the range 40:60 to 54:46;
in the manufacture of a low viscosity pre-formulation medicament for use in the in vivo formation of a depot for treatment of at least one condition selected from Cushing's disease, acromegaly, type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, e.g. morbid obesity or hypothalamic or hyperinsulinemic obesity, enterocutaneous and pancreaticocutaneous fistula, irritable bowel syndrome, inflammatory diseases, e.g. Grave's Disease, inflammatory bowel disease, psoriasis or rheumatoid arthritis, polycystic kidney disease, dumping syndrome, watery diarrhea syndrome, AIDS-related diarrhea, chemotherapy-induced diarrhea, acute or chronic pancreatitis and gastrointestinal hormone secreting tumors (e.g. GEP tumors, for example vipomas, glucagonomas, insulinomas, carcinoids and the like), lymphocyte malignancies, e.g. lymphomas or leukemias, hepatocellular carcinoma as well as gastrointestinal bleeding, e.g variceal oesophagial bleeding.

In all appropriate aspects of the invention, the preferred conditions are Cushing's disease and acromegaly.

One of the advantages of the formulations of the present invention over many other controlled-release compositions is that they are stable to storage in their final form and thus little or no preparation is required at the time of administration. This allows the pre-formulations to be ready-to-administer and also to be supplied in convenient, ready-to-administer form. In a further aspect, the invention therefore provides a pre-filled administration device containing a pre-formulation as described herein. Such a device will generally provide either a single administration or multiple administrations of a composition which will deliver, for example, a dosage of somatostatin receptor agonist in the range of 0.2 to 3 mg/day pasireotide.

In a further aspect the invention provides a kit comprising said administration device according to the invention.

The kit can optionally contain instructions for subcutaneous or intramuscular administration of said composition. All compositions described herein are suitable for use in such a kit and may thus be contained therein.

The kits of the invention can optionally include additional administration components such as needles, swabs, and the like and will optionally contain instructions for administration.

BRIEF SUMMARY OF THE ATTACHED FIGURES

FIG. 1. Flow chart describing the preparation of lipid/SOM230 (pasireotide) samples for solubility screening.

FIG. 2. Injectability (seconds/mL) measured at 20N constant force as a function of formulation composition and using 1 mL long Luer-Lock glass syringe with 23G ⅝" (16 mm) needle. The formulations numbers refer to the sample ID (last two digits) in Table 3. The data points represent the mean of duplicate measurements.

FIG. 3. Injectability (seconds per mL), measured at 20N constant force, as a function of formulation viscosity and using the indicated syringe and needle configuration.

FIG. 4. Comparison of stability data on lipid/pasireotide formulations differentiated by their respective solvent composition (SPC/GDO weight ratio constant at 50/50), with three different SOM230 (pasireotide) salt forms (pamoate (Pm), acetate (Ac) and hydrochloride (Cl)) after storage for 2 weeks at 60° C. The pasireotide free base concentration at start was in all cases approximately 30 mg/mL.

FIG. 5. Mean plasma concentrations of SOM230 (pasireotide pamoate) after s.c. injection in rats. The error bars denote standard deviation (n=6). Data obtained in PK-12-437.

FIG. 6. Mean plasma concentrations of SOM230 (pasireotide pamoate) after s.c. injection in rats. The error bars denote standard deviation (n=6). Data obtained in PK-12-438.

FIG. 7. Dose linearity with respect to exposure (AUC) in study PK-12-438. Error bars represent standard deviation.

FIG. 8. Dose linearity with respect to Cmax in study PK-12-438. Error bars represent standard deviation.

FIG. 9. Mean plasma concentrations of SOM230 (pasireotide pamoate) after s.c. injection in rats. The error bars denote standard deviation (n=6). Data obtained in PK-12-451.

FIG. 10. The SOM230 purity after storage at 5° C. The figure legend refers to the respective batch number as indicated in Table 19.

FIG. 11. The SOM230 purity after storage at 25° C./60% RH. The figure legend refers to the respective batch number as indicated in Table 19.

DETAILED DESCRIPTION OF THE INVENTION

The formulations of the present invention generate a non-lamellar liquid crystalline phase following administration. The use of non-lamellar phase structures (such as liquid crystalline phases) in the delivery of bioactive agents is now relatively well established. A most effective lipid depot system for general use is described in WO2005/117830, and a suitable lipid matrix for use in the present invention is described in general terms in that document, the full disclosure of which is hereby incorporated herein by reference. For a description of the most favourable phase structures of such formulations, attention is drawn to the discussion in WO2005/117830 and particularly to page 29 thereof.

All % are specified by weight herein throughout, unless otherwise indicated. Furthermore, the % by weight indicated is the % of the total pre-formulation including all of the components indicated herein where context allows. Weight percentages of pasireotide will be calculated on the basis of the weight of free acid irrespective of whether the acid or a salt thereof is used. The pre-formulations can optionally consist of essentially only the components indicated herein (including where appropriate additional optional components indicated herein below and in the attached claims) and in one aspect consist entirely of such components. Where a formulation is indicated as "consisting essentially of" certain components herein, when the specified components provide the essential nature of that formulation, such as when the specified components constitute at least 95%, preferably at least 98%, of the formulation.

The lipid-based systems described herein comprise lipid components a) and b), plus organic mono-alcoholic solvent (c), polar solvent (d), peptide somatostatin receptor agonist comprising pasireotide (e) and optional antioxidant (f) components.

Preferably the pre-formulation according to the invention is a molecular solution or has an $L_2$ phase structure (prior to administration). Preferably the pre-formulation forms a non-lamellar (e.g. liquid crystalline) phase following administration. Such a phase change is typically brought about by absorption of aqueous fluid from the physiological environment, as indicated herein.

The present inventors have now surprisingly established that by appropriate choice of types, absolute amounts and ratios of lipid components along with a peptide somatostatin receptor agonist comprising pasireotide and at least two solvents including an alcohol and at least one polar solvent, the release properties of the depot compositions formed from the pre-formulations of the invention can be rendered highly advantageous. In particular, by using a mixture of an alcohol and a polar solvent (especially at the weight ratios close to 1:1 described herein (e.g. between 10:1-1:3, preferably 5:1-1:2 and most preferably 2:1-2:3)) the advantages of the alcohol solvent on the release profile can be maintained while other properties such as the comfort on administration and/or the viscosity of the formulation can be improved. Alternatively or in addition to this, the release profile of the somatostatin receptor agonist can be made remarkably level, with the maximum plasma concentration in vivo being only a small multiple of the average or even minimum concentration during the dosing period. Such advantages apply even in comparison with other lipid depot compositions, which in themselves offer previously unobtainable standards in controlled release.

It is important, particularly with certain peptide active agents, such as somatostatin analogues (e.g. pasireotide), to control the peak concentration (Cmax) of drug in the plasma to a level equal to or less than that tolerable to the subject, for example to avoid side-effects such as flushing or severe nausea, while providing or achieving a therapeutically effective level over the desired period of release. Generally, the average concentration during the period of release before the next dose is administered, Cave, falls within the therapeutic range. Control over the maximal (Cmax) and minimum (Cmin) concentrations is also important in order to achieve the desired treatment over time. In one embodiment, the initial burst (e.g. during the first 12 hours following administration) is not the Cmax of the release profile.

Whether or not the initial burst is also the Cmax, preferably the Cmax/Cave ratio is less than 50, preferably less than or equal to 15, more preferably less than or equal to 10, even more preferably less than or equal to 5. Furthermore, it is preferred that the Cmax/Cmin ratio is not more than 50, preferably less than or equal to 15, more preferably less than or equal to 10, even more preferably less than or equal to 5. Cmax is defined as is known in the art, as the peak or maximal plasma concentration observed during the period of release before the next dose is administered and Cave is defined as the average plasma concentration during that period of release. Cmin is correspondingly the minimal concentration during that period. Cave can be calculated by calculating the drug present in the plasma as area under the curve (AUC) over the selected period of time, generally the entire period of release before the administration of the next dose, and dividing by that period of time.

Component a)—Diacyl Glycerol

Preferable ranges for component a) are 20-80 wt. %, preferably 30-70 wt. %, more preferably 20-50%, such as 33-60% (e.g. 43-60%, 30 to 43% or 30-40%), particularly 38 to 43%, around 32% (e.g. ±2) and/or around 40% (e.g. ±2). Preferable ranges of component b) are 20-80 wt. %, preferably 30-70 wt. % (e.g. 30-45%), more preferably 33-55% (e.g. 35-55%), particularly 38 to 43%.

Ratios of a:b are typically 40:60 to 70:30, preferably 45:55 to 55:45 and more preferably 40:60 to 54:46 or 42:58 to 48:52. Ratios of around 50:50 (e.g. ±2) and around 45:55 (e.g. ±3 a:b) are highly effective.

Component "a" as indicated herein is preferably at least one diacyl glycerol (DAG) and thus has two non-polar "tail" groups. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

Mixtures of any number of diacyl lipids may be used as component a). Preferably this component will include at least a portion of C18 lipids (e.g. DAG having one or more (i.e. one or two) C18:0, C18:1, C18:2 or C18:3 non-polar groups), such as glycerol dioleate (GDO) and/or glycerol dilinoleate (GDL). A highly preferred example is DAG comprising at least 50%, preferably at least 80% and even comprising substantially 100% GDO.

Since GDO and other diacyl glycerols are products derived from natural sources, there is generally a certain proportion of "contaminant" lipid having other chain lengths etc. In one aspect, GDO as used herein is thus used to indicate any commercial grade of GDO with concomitant impurities (i.e. GDO of commercial purity). These impurities may be separated and removed by purification but providing the grade is consistent this is rarely necessary. If necessary, however, "GDO" may be essentially chemically pure GDO, such as at least 80% pure, preferably at least 85% pure and more preferably at least 90% pure GDO.

Component b)—Phosphatidyl Choline

Component "b" in the preferred lipid matrices of the present invention is at least one phosphatidyl choline (PC). As with component a), this component comprises a polar head group and at least one non-polar tail group. The difference between components a) and b) lies principally in the polar group. The non-polar portions may thus suitably be derived from the fatty acids or corresponding alcohols considered above for component a. As with component a), the PC will contain two non-polar groups. Again, C18 groups are preferred and may be combined with any other suitable non-polar group, particularly C16 groups.

The phosphatidyl choline portion, even more suitably than any diacyl glycerol portion, may be derived from a natural source. Suitable sources of phospholipids include egg, heart (e.g. bovine), brain, liver (e.g. bovine) and plant sources including soybean. Such sources may provide one or more constituents of component b, which may comprise any mixture of phospholipids. Any single PC or mixture of PCs from these or other sources may be used, but mixtures comprising soy PC or egg PC are highly suitable. The PC component preferably contains at least 50% soy PC or egg PC, more preferably at least 75% soy PC or egg PC and most preferably essentially pure soy PC or egg PC.

In one embodiment applicable to all aspects of the invention, component b) comprises PC. Preferably the PC is derived from soy. Preferably the PC comprises 18:2 fatty acids as the primary fatty acid component with 16:0 and/or 18:1 as the secondary fatty acid components. These are preferably present in the PC at a ratio of between 1.5:1 and 6:1. PC having approximately 60-65% 18:2, 10 to 20% 16:0, 5-15% 18:1, with the balance predominantly other 16 carbon and 18 carbon fatty acids is preferred and is typical of soy PC.

In an alternative but equally preferred embodiment, also applicable to all aspects of the invention, the PC component may comprise synthetic dioleoyl PC. This is believed to provide increased stability and so will be particularly preferable for compositions needing to be stable to long term storage, and/or having a long release period in vivo. In this embodiment the PC component preferably contains at least 50% synthetic dioleoyl PC, more preferably at least 75% synthetic dioleoyl PC and most preferably essentially pure synthetic dioleoyl PC. Any remaining PC is preferably soy or egg PC as above.

In one embodiment, the precursor formulations of the present invention are comprised at least partially of synthetic DOPC (i.e. PC having at least 95% PC head groups and at least 90% oleoyl acyl groups) and has a stability to storage at 15-25° C., defined as less than 5% peptide degradation as assayed by peptide purity, of at least 6 months, more preferably at least 12 months and most preferably at least 24 months.

Since the pre-formulations of the invention are to be administered to a subject for the controlled release of a peptide active agent, it is important that the components are biocompatible. In this regard, the preferred lipid matrices for use in the pre-formulations of the present invention are highly advantageous since both PC and DAGs are well tolerated and are broken down in vivo into components that are naturally present in the mammalian body.

Synthetic or highly purified PCs, such as dioleoyl phosphatidylcholine (DOPC) and palmitoyl oleoyl phosphatidylcholine (POPC), as well as the other various high-purity PCs described herein, are highly appropriate as all or part of component b).

In a highly preferred embodiment, component b) is a "high purity" PC as follows: b. at least one phospholipid component comprising phospholipids having
  i. polar head groups comprising at least 95% phosphatidyl choline, and
  ii. two acyl chains each independently having 16 to 20 carbons wherein at least one acyl chain has at least one unsaturation in the carbon chain, and there are no more than four unsaturations over two carbon chains;

Typically, this may be PC with at least 95% PC head groups and at least 95% C16 to C20 acyl chains having 0 to 3 unsaturations.

The synthetic dioleoyl PC is most preferably 1,2-dioleoyl-sn-glycero-3-phosphocholine, and other synthetic PC components include DDPC(1,2-Didecanoyl-sn-glycero-3-phosphocholine); DEPC(1,2-Dierucoyl-sn-glycero-3-phosphocholine); DLOPC(1,2-Dilinoleoyl-sn-glycero-3-phosphocholine); DLPC(1,2-Dilauroyl-sn-glycero-3-phosphocholine); DMPC(1,2-Dimyristoyl-sn-glycero-3-phosphocholine); DOPC(1,2-Dioleoyl-sn-glycero-3-phosphocholine); DPPC(1,2-Dipalmitoyl-sn-glycero-3-phosphocholine); DSPC(1,2-Distearoyl-sn-glycero-3-phosphocholine); MPPC(1-Myristoyl-2-palmitoyl-sn-glycero 3-phosphocholine); MSPC(1-Myristoyl-2-stearoyl-sn-glycero-3-phosphocholine); PMPC(1-Palmitoyl-2-myristoyl-sn-glycero-3-phosphocholine); POPC(1-Palmitoyl-2-oleoyl-sn-glycero-3-phosphocholine); PSPC(1-Palmitoyl-2-stearoyl-sn-glycero-3-phosphocholine); SMPC(1-Stearoyl-2-myristoyl-sn-glycero-3-phosphocholine); SOPC(1-Stearoyl-2-oleoyl-sn-glycero-3-phosphocholine); and SPPC(1-Stearoyl-2-palmitoyl-sn-glycero-3-phosphocholine), or any combination thereof.

In some circumstances, such as the absence of preserving agents such as EDTA, the use of synthetic or highly purified PCs (e.g. DOPC) may provide greater stability for the somatostatin receptor agonist in the formulations. Thus in one embodiment, component b) may comprise (e.g. may comprise at least 75%) synthetic or highly purified (e.g. purity >90%) PCs (e.g. DOPC). This may particularly be in the absence of chelating agents such as EDTA. In an alternative embodiment, component b) may comprise (e.g. comprise at least 75%) naturally derived PCs, such as soy PC or egg PC. This will particularly be where at least one stabilising component (such as an antioxidant, chelator etc) is included in the precursor formulation.

A particularly favoured combination of components a) and b) are GDO with PC, especially GDO with soy PC and/or "high purity" PC. Appropriate amounts of each component suitable for the combination are those amounts indicated herein for the individual components in any combination. This applies also to any combinations of components indicated herein, where context allows.

The ratio of components a:b is in the range 40:60 to 54:46. Preferably the a:b ratio is in the range 45:55 to 54:46, more preferably 47:53 to 53:47. Most preferably the a:b ratio is approximately 50:50.

In one embodiment applicable to all aspects of the invention, it is preferred if the a:b ratio is in the range 40:60 to 49:51. In an alternative embodiment, the ratio may be in the range 42:58 to 52:48.

Component c)—Organic Mono-Alcoholic Solvent

Component c) of the pre-formulations of the invention is an organic mono-alcoholic solvent. Since the pre-formulation is to generate a depot composition following administration (e.g. in vivo), typically upon contact with excess aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

Most preferably component c) comprises or consists of ethanol, propanol, ispropanol, benzyl alcohol or mixtures thereof. Most preferably component c) comprises or consists of ethanol.

In a preferred embodiment, the solvent is such that a relatively small addition to a mixture comprising a) and b) (i.e. preferably below 15%) gives large viscosity reductions, of one order of magnitude or more. As described herein, the addition of 10% organic mono-alcohol solvent can give a reduction of two or more orders of magnitude in viscosity over the solvent-free composition, or over a depot containing only a polar solvent such as water, or glycerol.

The amount of component c) in the pre-formulation will have a considerable effect upon several features. In particular, the viscosity and the rate (and duration) of release will alter significantly with the solvent level. The amount of solvent will thus be at least sufficient to provide a low viscosity mixture but will additionally be determined so as to provide the desired release rate. This may be determined by routine methods in view of the Examples below. Typically a level of 0.1 to 35%, particularly 5 to 25% solvent will provide suitable release and viscosity properties. This will preferably be 5 to 16% (e.g. 6 to 14%) and an amount of around 8% (e.g. 8±2%) is highly effective.

As indicated above, the amount of component c) in the pre-formulations of the invention will be at least sufficient to provide a low viscosity mixture (e.g. a molecular solution, see above) of components a), b), c) and d) and optionally f)

and will be easily determined for any particular combination of components by standard methods.

The phase behaviour may be analysed by techniques such as visual observation in combination with polarized light microscopy, X-ray scattering and diffraction techniques, nuclear magnetic resonance, and cryo-transmission electron microscopy (cryo-TEM) to look for solutions, $L_2$ or $L_3$ phases, or liquid crystalline phases or as in the case of cryoTEM, dispersed fragments of such phases. Viscosity may be measured directly by standard means. As described above, an appropriate practical viscosity is that which can effectively be syringed and particularly sterile filtered. This will be assessed easily as indicated herein.

Typical organic mono-alcoholic solvents suitable for use in the invention include at least one solvent selected from ethanol, propanol, isopropanol, and benzyl alcohol, particularly ethanol.

A highly preferred combination for components a), b) and c) is soy PC and/or "high purity PC", GDO and ethanol. As indicated above, appropriate amounts of each component suitable for the combination are those amounts indicated herein for the individual components, in any combination.

It is preferable that little or none of component c) contains halogen substituted hydrocarbons since these tend to have lower biocompatibility. For example, the content of halogenated organic solvents may be less than 0.5%, preferably less than 0.1%.

Component c) as used herein may be a single solvent or a mixture of suitable solvents but will generally be of low viscosity. This is important because one of the key aspects of the present invention is that it provides pre-formulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c) (single solvent or mixture) should typically be no more than 18 mPas at 20° C. This is preferably no more than 15 mPas, more preferably no more than 10 mPas and most preferably no more than 7 mPas at 20° C.

Component d)—Polar Solvent

Some of the particular benefits of the compositions of the present invention come through the unexpected finding that the use of an alcohol solvent in combination with a polar solvent such as a diol or water allows a significant improvement in the performance of certain lipid-based controlled-release compositions. In particular, the addition of a diol (such as propylene glycol) or water has been observed to allow the proportion of alcohol to be increased without adversely affecting the release profile and/or allow an improvement in the release profile and/or allow higher loading of the somatostatin receptor agonist. By "adversely affecting the release profile" is intended to indicate that the ratio of Cmax/Cave is increased and/or the ratio of Cmax/Cmin is increased (for example increased by a factor of at least 1.2). Similarly an improvement in the release profile indicates that the ratio of Cmax/Cave and/or Cmax/Cmin is decreased (e.g. decreased by a factor of at least 1.2.).

Typical polar solvents will have a comparatively high dielectric constant corresponding to their high polarity. Thus, suitable polar solvents will generally have a dielectric constant of at least 28 at 25° C., more preferably at least 30 at 25° C. Highly suitable examples include water (~80), propylene glycol (~32) and N-methyl-2-pyrrolidone (NMP, ~32).

Although it has previously been suggested that lipid controlled-release compositions should be formulated substantially in the absence of water, in order to avoid the conversion to high-viscosity liquid crystalline phases, it has now furthermore been established that a small and carefully controlled amount of a polar solvent such as water can provide considerable benefits. In particular, the inclusion of this polar solvent (preferably comprising water) allows further improvements in controlling the initial release of somatostatin receptor agonist, allows higher stable loading of some peptide somatostatin receptor agonists, provides faster depot formation and/or provides further reduced discomfort upon injection. Any one of these factors potentially provides a significant improvement in the context of therapeutic drug delivery, patient health and/or patient compliance.

The pre-formulations of the present invention must thus also contain a polar solvent, component d). A suitable amount will typically be greater than 1% by weight of the pre-formulation, for example 1-30 wt. %, particularly 1.2-20 wt. %, especially 2-18 wt. %. More preferably component d) is present in the range 5-15 wt. %, especially 6-12 wt. %. Component d) is preferably water, propylene glycol or mixtures thereof. In one preferred aspect, the pre-formulations of the invention contain ethanol as component c) with water and/or propylene glycol as component d).

In one embodiment the pre-formulation comprises at least 1.5% (e.g. at least 4.5%) water as part of component d) (by weight of the total composition) with the remainder being propylene glycol. At least 5% water with the balance of component d) being PG is preferred. Component d) may comprise or consist of water.

In an alternative embodiment, component d) may comprise or consist of propylene glycol.

Preferably the total level of components c) and d) is not more than 35 wt. %, preferably not more than 30 wt. %, more preferably not more than 25 wt. %, most preferably not more than 20 wt. %. For example the total level of components c) and d) may be in the range 10-30 wt. %, preferably 12-25 wt. %, most preferably 15-20 wt. %.

The ratio of components c) and d) will also have potential advantages in the compositions of the invention. In particular, by inclusion of some polar solvent which is miscible with the mono-alcohol component (especially water), the slight sensation that may be caused at the injection site from the alcohol content can be substantially eliminated. Thus, in one embodiment, the ratio of components c):d) may be in the range 30:70 to 70:30, more preferably 40:60 to 60:40. In one embodiment, the amount of alcohol component c) by weight is no greater than the amount of polar solvent d). Ratios of c):d) ranging from 30:70 to 50:50 are thus appropriate in such an embodiment. Approximately equal amounts of components c) and d) are highly appropriate.

A highly preferred combination for the lipid matrix aspect is soy PC and/or a C16 to C20 PC of at least 95% purity such as DOPC (as described herein), with GDO, ethanol, and water/propylene glycol or mixtures thereof. The solvent may be, for example, ethanol and water in the absence of PG, ethanol and PG in the absence of water, or a mixture of all three. As indicated above, appropriate amounts of each component suitable for the combination are those amounts indicated herein for the individual components, in any combination.

Component e)—Peptide Active Agent (Somatostatin Receptor Agonist)

The pre-formulations of the present invention contain at least one peptide somatostatin receptor agonist comprising pasireotide. Suitable peptides for use in the necessary peptide somatostatin receptor agonists may be naturally occurring or derived from natural peptides, or may be chemically modified or wholly synthetic peptide molecules. Any amino acids may be comprised in the peptides including those described herein, and the peptides may be chemically or enzymatically modified. Similarly, peptide somatostatin receptor agonists may be linear or cyclised by means of one or more covalent or non-covalent interactions. Pasireotide, for example, comprises a cyclic portion of six peptide residues (see below).

Typical peptide actives will be in the range of 500 to 100,000 amu in molecular weight and can evidently include protein somatostatin receptor agonists. In one embodiment, the polypeptides can have at least one cationic charge at neutral and/or physiological pH, and most preferably will require at least one anionic counter-ion at pH 6.5 or above, preferably at pH 7.5 or above. This counter-ion will be physiologically acceptable, and may thus be a halide or the ion of a physiologically acceptable acid. Acetate, pamoate and tartrate counter ions and/or chloride ions are particularly preferred and therefore in one embodiment of the invention, the somatostatin receptor agonist is pasireotide pamoate.

In particular, the present inventors have surprisingly established that pasireotide pamoate is surprisingly more stable to storage when formulated with the lipid excipients described herein than is the corresponding acetate or chloride salt. This is particularly surprising since the acetate is the most commonly used form of many small peptide active agents, such as the somatostatin analogue octreotide. Furthermore, the chloride salt has been shown in previous work to be surprisingly effective in formulations of certain actives, such as octreotide. However, in the present case, storage at 60° C. in formulations of the present invention illustrated a markedly higher stability for the pamoate over the acetate and even the chloride of pasireotide (see examples and Figures below). The pamoate salt is thus the preferred form of the somatostatin receptor agonist comprising pasireotide.

In the peptide actives of the present invention, peptides may contain only amino acids selected from those 20 α-amino acids indicated in the genetic code, or more preferably may contain their isomers and other natural and non-natural amino acids, (generally α, β or γ amino acids) and their analogues and derivatives.

Amino acid derivatives are especially useful at the termini of the peptides, where the terminal amino or carboxylate group may be substituted by or with any other functional group such as hydroxy, alkoxy, carboxy (on the N-terminal end), ester, amide, thio, amido, amino (on the C-terminal end), alkyl amino, di- or tri-alkyl amino, alkyl (by which is meant, herein throughout $C_1$-$C_{20}$ alkyl, preferably $C_1$-$C_{18}$ alkyl e.g. methyl, ethyl, n-propyl, isopropyl, n-butyl, iso-, sec- or t-butyl etc.), aryl (e.g phenyl, benzyl, napthyl etc), heteroaryl, or other functional groups, preferably with at least one heteroatom and preferably having no more than 20 atoms in total, more preferably no more than 10 and most preferably not more than 6 atoms (optionally excluding hydrogens).

In the present invention, the peptide somatostatin receptor agonist comprises pasireotide, which is a somatostatin analogue. The somatostatin receptor agonist may also comprise other peptides such as other peptide analogues of somatostatin and may include octreotide, somatostatin 14 and/or somatostatin 28.

Somatostatin has two active forms produced by alternative cleavage of a single preprotein: one of 14 amino acids, the other of 28 amino acids. Somatostatin 1-14 is a cyclic peptide hormone having the sequence Ala-Gly-Cys-Lys-Asn-Phe-Phe-Trp-Lys-Thr-Phe-Thr-Ser-Cys (SEQ ID NO: 1), where the two cysteine residues are connected by a disulphide bridge to generate a type II β-turn at the key binding sequence of Phe-Trp-Lys-Thr (SEQ ID NO: 2) . . . . Somatostatin is a natural peptide hormone also known as Growth Hormone Release Inhibiting Factor and has a role as an antagonist of insulin, glucogen and certain other hormones in the release of somatotrophin (Human Growth Hormone). The biological half-life of natural Somatostatin is very short (1-3 minutes) and so in itself is difficult to formulate as a viable therapeutic. However, the lipid depot compositions of the present invention are highly effective for short-lived active agents and an increasing number of somatostatin analogues are becoming available with higher activities and/or longer clearance times in vivo. Pasireotide is one such analogue and forms the essential peptide active agent of the compositions of the present invention.

Somatostatin analogues, including pasireotide, but also such as octreotide, lanreotide, vapreotide and related peptides, are used or indicated in the treatment of a variety of conditions where they are typically administered over an extended period. In one embodiment of the invention, the peptide active agent comprises or consists of pasireotide as well as another somatostatin analogue selected from the group consisting of octreotide, lanreotide and vapreotide. In one embodiment, the peptide active agent of the invention comprises or consists of pasireotide and octreotide. In a further embodiment, pasireotide may form the sole active agent.

Octreotide, for example, is the synthetic octa-peptide with sequence D-Phe-Cys-Phe-D-Trp-Lys-Thr-Cys-Thr-ol (2-7 disulphide bridge) and is typically administered as the acetate salt. Several clinical studies also feature the octreotide pamoate. This derivative retains the key Phe-(D)Trp-Lys-Thr β-turn but, in contrast to the natural hormone, has a terminal half-life of around 1.7 hours. Octreotide is used in treatment of conditions including carcinoid tumours and acromegaly, and after an initial dose is typically given over a sustained period of weeks, or more commonly many months or years. In addition, somatostatin analogues are indicated in the treatment of many cancers since a wide variety of tumours are found to express somatostatin receptors. Of particular interest are those expressing the "sst(2)" and/or "sst(5)" receptor.

As used herein, the term "somatostatin receptor agonist" is used to indicate a compound having an agonistic function at one or more somatostatin receptors (SSTRs). There are five known types of SSTRs (SSTR1-SSTR5), showing equally high affinity for SST-14. The most investigated somatostatin receptor agonists, including octreotide, show high selectivity for SSTR2 and SSTR5. Thus in one preferred embodiment, somatostatin receptor agonists as indicated herein have an agonistic function at somatostatin receptors including SSTR2 and/or SSTR5.

The most common "simple" formulation of Octreotide is "Sandostatin" ® from Novartis. This is a solution for subcutaneous (s.c) injection and a 100 μg dose reaches a peak concentration of 5.2 ng/ml at 0.4 hours post injection. The duration of action can be up to 12 hours but s.c. dosing is generally carried out every 8 hours. Evidently, s.c. injection 3 times daily for periods of months or years is not an ideal dosing regime.

In order to avoid the need for multiple daily injections of octreotide, a further formulation is available; "Sandostatin LAR"®, again from Novartis. This is a formulation of octreotide in poly lactic co-glycolic acid microspheres which, after reconstitution in an aqueous diluent, may be administered by intra muscular (i.m.) injection.

Pasireotide is a multireceptor-targeted somatostatin analogue with high affinity for somatostatin receptor subtypes sstr1,2,3 and sstr5 that has been developed for the treatment of neuroendocrine diseases. Two formulations of pasireotide have currently been developed: an immediate-release formulation for subcutaneous (sc) injection and a long-acting-release (LAR) formulation. The structure of pasireotide is as follows:

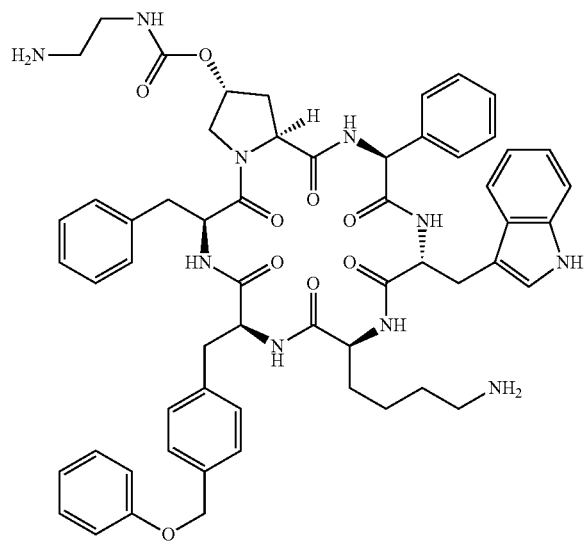 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(COc3ccccc3)cc2)NC1=O]

Pasireotide was initially developed by Novartis Pharma as a treatment for Cushing's disease/syndrome and acromegaly, but has potential applicability in the treatment of several conditions for which somatostatin analogues such as octreotide are indicated, including carcinoid tumours.

Following a single subcutaneous dose of pasireotide, human plasma levels typically peak quickly, at around 15 minutes to 1 hour after dosing, with an initial half-life of 2-3 hours following that peak. Although clearance half-life is greater for later phases of the decline, it is clear that the Cmax/Cave for such a delivery will be rather high.

Pasireotide LAR is a long acting formulation of pasireotide which addresses some of the above issues. However, this is a polymer microparticle based system with the inherent limitations of such a system, as are known in the art and described herein above.

Carcinoid tumours are intestinal tumour arising from specialised cells with paracrine functions (APUD cells). The primary tumour is commonly in the appendix, where it is clinically benign. Secondary, metastatic, intestinal carcinoid tumours secrete excessive amounts of vasoactive substances, including serotonin, bradykinin, histamine, prostaglandins, and polypeptide hormones. The clinical result is carcinoid syndrome (a syndrome of episodic cutaneous flushing, cyanosis, abdominal cramps, and diarrhea in a patient with valvular heart disease and, less commonly, asthma and arthropathy). These tumours may grow anywhere in the gastrointestinal tract (and in the lungs) with approximately 90% in the appendix. The remainder occurs in the ileum, stomach, colon or rectum. Currently, treatment of carcinoid syndrome starts with i.v. bolus injection followed by i.v. infusion. When sufficient effect on symptoms has been established, treatment with a depot formulation of octreotide formulated in poly lactic-co-glycolic acid (PLGA) microspheres is started. However, during the first two weeks or more after injection of the depot, daily s.c. injections with octreotide are recommended to compensate for the slow release from the PLGA spheres.

Acromegaly is a rare chronic and insidious hormonal disorder that occurs when the pituitary gland produces excess growth hormone (GH). It most commonly affects middle-aged adults and may lead to premature death.

Diabetes mellitus, hypertension, and increased risk of cardiovascular disease are the most serious health consequences of acromegaly. In addition, patients with acromegaly are at an increased risk of developing colon polyps, which can become cancerous. The prevalence of acromegaly is approximately 60 cases per million population, and the incidence is 3.3 new cases per million per year. The word acromegaly comes from the Greek words for "extremities" (acro) and "great" (megaly), because one of the most common symptoms of this condition is abnormal growth of the hands and feet.

Acromegaly is caused by prolonged overproduction of growth hormone (GH) and excessive production of insulin-like growth factor-I (IGF-I). In 98 percent of cases, the overproduction of GH is caused by a pituitary adenoma. The rate of GH production and the aggressiveness of the tumour vary from patient to patient. Generally, more aggressive tumours are seen in younger patients.

Acromegaly is a severe disease often diagnosed late. Morbidity and mortality rates are high, in particular, because of associated cardiovascular, cerebrovascular, and respiratory disorders and malignancies.

Current treatment of acromegaly is typically initiated by a period of s.c. injections three times per day (optimal daily dose=300 μg octreotide). After the last s.c. dose and providing a suitable effect is observed then treatment with a depot formulation of octreotide formulated in poly lactic-co-glycolic acid (PLGA) microspheres is started. Dose adjustments are made after measurement of biomarkers (HG and IGF-1), typically after around 3 months.

The existing octreotide slow release formulation relies upon a well-established degrading-polymer type of depot formulation. Typically such formulations are based on a biodegradable polymer such poly (lactic acid) (PLA) and/or poly (lactic-co-glycolic acid) (PLGA) and may be in the form of a solution in an organic solvent, a pre-polymer mixed with an initiator, encapsulated polymer particles or (as in the case of octreotide) polymer microspheres.

In one typical embodiment, the peptide somatostatin receptor agonist comprising pasireotide will generally be formulated as 0.02 to 12% by weight of the total formulation. Typical values will be 0.1 to 10%, preferably 0.2 to 8%, more preferably 0.5 to 6% (e.g. 1 to 3%). These levels may be applied to all aspects of the invention, where context allows. A further preferred range is between 0.5 to 4 wt. %, more preferably 1-3 wt. %, and most preferably 1.5-2.5 wt. %.

In one embodiment of the present invention, the concentration of Pasireotide in the precursor formulations of the present invention is greater than 4% and the ratio of components a)/b) is less than 1. That is to say the weight percentage of component a) is less than that for component b). In particular, in this embodiment of high Pasireotide content, the ratio of a) to b) may be between 49:51 and 40:60, preferably 48:52 to 42:58.

In a related embodiment, the peptide somatostatin receptor agonist may be formulated at a level which cannot easily be achieved in the absence of the polar solvent component of the mixture. In such an embodiment, the pasireotide content is typically at least 0.7%, preferably at least 1%, more preferably at least 1.8% or at least 2% by weight of formulation. Levels of at least 3% and at least 4% are achievable with the present invention, as are loading levels up to 8, 10 or 12%. Such compositions of the present invention typically not only contain a very high level of peptide somatostatin receptor agonist as indicated, but are additionally stable to storage with no or low degradation of the somatostatin receptor agonist (e.g. less than 5%) for considerable periods, as indicated herein. Such periods will generally be at least a month at 25° C. or at least a month at 5° C., preferably at least 3 months, more preferably at least 6 months, most preferably 12 to 24 months at 5° C. or alternatively at 25° C. These degrees of stability are applicable to all aspects of the invention, where context allows and relate to stability both of the somatostatin receptor agonist and of the phase behaviour of the pre-formulation.

In a related embodiment, in the situation where a peptide somatostatin receptor agonist is highly soluble in the alcohol component, it may be an advantage to limit this solubility of this agent. Without being bound by theory, it is thought that excessive solubility in this alcohol component may result in the alcohol transporting a significant quantity of somatostatin receptor agonist out of the depot composition as it forms in vivo. Therefore, in one embodiment of the present invention, the polar solvent is used to control the solubility of the somatostatin receptor agonist in the pre-formulation so as to aid control of the release profile.

In a further aspect, the present invention therefore provides a method for controlling the solubility of a peptide somatostatin receptor agonist comprising pasireotide in a low viscosity mixture comprising:
  a) 20-50 wt. % of at least one diacyl glycerol;
  b) 20-54 wt. % of at least one phosphatidyl choline (PC);
  c) 5-15 wt. % of at least one biocompatible, organic mono-alcoholic solvent;
  e) 5 to 150 mg/ml of at least one peptide somatostatin receptor agonist comprising pasireotide;
  f) optionally at least one antioxidant;
by inclusion of a polar solvent component d) to form a depot precursor formulation. Use of a polar solvent in such a method forms a further aspect.

The pre-formulations and components of the mixture, as well as their performance etc will evidently correspond to those described herein for other aspects.

Similarly, the present invention provides a method for improving the release profile of a peptide somatostatin receptor agonist comprising pasireotide from a depot composition formed by injection of a low viscosity mixture comprising:
  a) 20-50 wt. % of at least one diacyl glycerol;
  b) 20-54 wt. % of at least one phosphatidyl choline (PC);
  c) 5-15 wt. % of at least one biocompatible, organic mono-alcoholic solvent;
  e) 5 to 150 mg/ml of at least one peptide somatostatin receptor agonist comprising pasireotide;
  f) optionally at least one antioxidant;
by inclusion of a polar solvent component d) in said low-viscosity mixture to form a depot precursor formulation. Use of a polar solvent in such a method forms a further aspect.

The pre-formulations and components of the mixture, as well as their performance etc will evidently correspond to those described herein for other aspects.

Corresponding methods and uses provide for the reduction of injection-site discomfort, reduction of viscosity of the pre-formulation, and/or reduction in initial "burst" release of a low viscosity mixture comprising:
  a) 20-50 wt. % of at least one diacyl glycerol;
  b) 20-54 wt. % of at least one phosphatidyl choline (PC);
  c) 5-15 wt. % of at least one biocompatible, organic mono-alcoholic solvent;
  e) 5 to 150 mg/ml of at least one peptide somatostatin receptor agonist comprising pasireotide;
  f) optionally at least one antioxidant;
by inclusion of a polar solvent component d) in said low-viscosity mixture to form a depot precursor formulation. Use of a polar solvent in such a method forms a further aspect.

All of the above uses and methods for improving the various properties of the pre-formulation and/or the resulting depot composition are preferably applied without negatively affecting the release profile of the peptide somatostatin receptor agonist.

The peptide somatostatin receptor agonist comprises pasireotide, hence suitable doses for inclusion in the formulation, and thus the volume of formulation used, will depend upon the release rate (as controlled, for example by the solvent type and amount used, the antioxidant content and so forth) and release duration, as well as the desired therapeutic level, the activity of the specific agent, and the rate of clearance of the particular active chosen. Typically an amount of around 0.05 to 40 mg per week of depot duration, preferably 0.1 to 20 mg per week duration (e.g. 1 to 5 mg per week) for a duration of 1 to 24 weeks, preferably 2 to 16 (e.g. 3, 4, 8, 10 or 12) weeks. In an alternative embodiment the pre-formulation may be formulated for dosing weekly (e.g. every 7±1 days). A total dose of 0.05 to 250 mg per dose would be suitable for providing a therapeutic level for between 7 and 168 days. This will preferably be 0.1 to 200 mg, e.g. 0.2 to 150 mg, 0.1 to 100 mg, 20 to 160 mg etc. Evidently, the stability of the active and effects on the release rate will mean that the loading to duration may not be a linear relationship. A depot administered every 30 days might have, for example 0.2 to 20 mg, or a 90 day depot might have 30 to 60 mg of somatostatin receptor agonist.

Evidently also, the biological half-life of the specific active will be particularly important. The half-life of somatostatin, is less than 5 minutes, and so for sustained release, a relatively large amount (e.g. towards the higher end of the range) will be needed. For an analogue such as pasireotide, with a much longer half-life (2-3 hours at least), the amount needed will evidently be lower. Appropriate levels for the specific actives will be established easily by those of skill in the art by reference to the known therapeutic level, the desired duration of action and the volume which is to be injected. A good base calculation would be to multiply a typical daily dose of the active agent by the number of days' duration of the depot. The formulation can then be tested for linearity of release and adjusted as appropriate.

In a highly preferred embodiment, the lipid matrix aspect is soy PC or "high purity" PC (such as DOPC), GDO, ethanol, and water/propylene glycol or mixtures thereof, and the peptide somatostatin receptor agonist comprises pasireotide. As indicated above, appropriate amounts of each component suitable for the combination are those amounts indicated herein for the individual components, in any combination.

In one preferred embodiment, GLP-1, GLP-1 analogues and GLP-1 receptor agonists and/or GLP-1 receptor antagonists are not present in the precursor formulations of the invention.

Optional Component f)—Antioxidant

Component f) is an antioxidant. Most preferably it is selected from ascorbic acid, ascorbyl palmitate, ethylenediaminetetraacetic acid (EDTA) and salts thereof and citric acid.

In all aspects of the invention, component f) is typically present at a weight ratio of antioxidant to peptide somatostatin receptor agonist of 1:50 to 1:6000, preferably 1:100 to 1:1300, and most preferably 1:150 to 1:1250. Since typical antioxidants are of lower molecular weight that the peptide somatostatin receptor agonists, the proportion by weight of antioxidant may be relatively small. For example, with a small molecular weight antioxidant (e.g. less than 500 amu), 0.0001 to 0.5% of the composition may be antioxidant, preferably 0.0005 to 0.2%, more preferably 0.0008 to 0.1%, e.g. 0.001 to 0.02%.

Unfortunately, many common antioxidants are not highly compatible with lipid systems. Indeed, the present inventors have previously established that some antioxidants commonly used in previous systems can cause increased degradation of active agents in a lipid system. This applies particularly to peptide active agents. The present inventors have therefore analysed a variety of potential antioxidant compounds and classes for use with lipid based matrix systems and have surprisingly found that one particular class of antioxidants is unusually well suited for use in these systems.

The antioxidant component is generally included in the range 0.0001 to 0.5% by weight of the total pre-formulation. Around 0.0005 to 0.015% of antioxidant (particularly EDTA) is particularly preferred, especially in combination with the other preferred components and ranges indicated herein above and below.

Stability data using a number of different antioxidants demonstrate that EDTA antioxidants are surprisingly more efficient than other antioxidants in suppressing the oxidative degradation of bioactive agents. EDTA as antioxidant can also show a synergistic effect in combination with the antioxidants of the present invention, in maintaining the chemical and physical stability of the peptide active agent and complete pre-formulation. EDTA has a stabilising effect on the active agent.

By "stabilising" is indicated an increase in the physical and chemical stability of the dissolved or dispersed somatostatin receptor agonist. An increase in stability may be demonstrated by the chemical and/or physical stability of a peptide somatostatin receptor agonist in a lipid formulation for a greater period than would be observed in the absence of an antioxidant. This would preferably be tested under conditions of typical storage, such as 2-8° C., 25° C. and/or ambient temperature. This is further described herein below.

In a preferred embodiment of the invention, antioxidants are excluded from the pre-formulations.

Optional Additional Components

In one particularly preferred embodiment of the present invention, the compositions (preformulations and resulting depots) do not include fragmentation agents, such as polyethyleneoxide or poly(ethylene glycol) (PEG) fragmentation agent, e.g. a PEG grafted lipid and/or surfactant.

For example, the compositions preferably do not include fragmentation agents such as Polysorbate 80 (P80, polyoxyethylene (20) sorbitan monooleate), or other Polysorbates (e.g. Polysorbate 20), PEGylated phospholipids (PEG-lipids such as DSPE-PEG(2000), DSPE-PEG(5000), DOPE-PEG (2000) and DOPE-PEG(5000)), Solutol HS 15, PEGylated fatty acids (e.g. PEG-oleate), block co-polymers such as Pluronic® F127 and Pluronic® F68, ethoxylated castor oil derivatives (e.g. Chremophores), PEGylated glyceryl fatty acid esters (such as TMGO-15 from Nikko Chemicals) and PEGylated tocopherols (such as d-alpha tocopheryl poly (ethylene glycol)1000 succinate known as Vitamin E TPGS from Eastman.

Single-dose formats must remain stable and potent in storage prior to use, but are disposable after the single use. In one embodiment, a single dose format is stable at refrigerated conditions (e.g. 0-5 or 2-8° C.) for at least 12 months. Furthermore such a pre-formulation may be stable at room temperature (e.g. 25° C.) for at least 12 months. Multi-dose formats must not only remain stable and potent in storage prior to use, but must also remain stable, potent and relatively free of bacteria (and particularly essentially free of bacterial growth) over the multiple-dose use regimen administration period after the first use in which a seal has been compromised. For this reason multi-dose formats often require an anti-microbial or microbial-static agent, e.g. bacteriostatic agent, preservative.

However, the production of preserved pharmaceutical preparations containing protein or peptide actives has often proven difficult, as when preservatives are used, these give rise to stability problems. Often the proteins are inactivated and aggregates are formed, which may sometimes lead to reported injection site intolerance or immunogenicity to the active. This can be further aggravated by additional excipients or formulation components.

In one aspect each of the embodiments herein can optionally contain an antimicrobial or microbial-static agent, which includes bacteriostatic agents and preservative. Such agents include benzalkonium chloride, m-cresol, benzyl alcohol or other phenolic preservatives. Typical concentrations as known in the art can be used.

Additional components above those mentioned as components a) to f) will, where present at all, preferably be present in an amount of 0 to 5% (e.g. 0.01% to 5%) by weight, preferably no more than 2% by weight and more preferably no more than 1% by weight.

In one embodiment, components a) and b) (allowing for any impurity inherent in the nature of these components) make up at least 95% of the lipid components of the composition. Preferably at least 99% of the total lipid content of the pre-formulation consists of components a) and b). Preferably the lipid component of the pre-formulation consists essentially of components a) and b).

Administration

The pre-formulations of the present invention are generally formulated to be administered parenterally. This administration will generally not be an intra-vascular method but will preferably be subcutaneous (s.c.), intracavitary or intramuscular (i.m.). Typically the administration will be by injection, which term is used herein to indicate any method in which the formulation is passed through the skin, such as by needle, catheter or needle-less (needle-free) injector. Preferred parenteral administration is by i.m or s.c. injection, most preferably by s.c. injection. An important feature of the composition of the invention is that it can be administered both by i.m. and s.c. and other routes without toxicity or significant local effects. It is also suitable for intracavital administration. The s.c. injection has the advantage of being less deep and less painful to the subject than the (deep) i.m. injection used for some current depots and is technically most suitable in the present case as it combines ease of injection with low risk of local side effects. It is a surprising observation of the present inventors that the formulations provide sustained release of active agent over a predictable time period by both subcutaneous and intramuscular injection. This therefore allows the site of injection to be varied widely and allows the dose to be administered without detailed consideration of the tissue depth at the site of injection.

The preferred lipid pre-formulations of the present invention provide non-lamellar liquid crystalline depot compositions upon exposure to aqueous fluids, especially in vivo. As used herein, the term "non-lamellar" is used to indicate a normal or more preferably reversed liquid crystalline phase (such as a reversed cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise. The skilled reader will have no difficulty in identifying those compositions having appropriate phase behaviour by reference to the description and Examples provided herein, and to WO2005/117830, but the most favoured compositional area for phase behaviour is where ratio of components a:b are in the region of 40:60 to 70:30, preferably 45:55 to 55:45 and more preferably 40:60 to 54:46. Ratios of around 50:50 (e.g. ±2) are highly preferred for most formulations (although certain exceptions are noted herein), most preferably around 50:50.

It is important to appreciate that the pre-formulations of the present invention are of low viscosity. As a result, these pre-formulations must not be in any bulk liquid crystalline phase since all liquid crystalline phases have a viscosity significantly higher than could be administered by syringe or similar injecting dispenser. The pre-formulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 5 wt %, preferably greater than 7%, and most preferably greater than 9% of organic mono-alcoholic solvent (component c) having a viscosity reducing effect. The pre-formulations of the invention which are in $L_2$ phase form one preferred set of pre-formulations and these will generally contain at least 2% water as polar solvent.

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a small gauge needle. Preferably, the low viscosity mixtures can be dispensed through a needle of 19 gauge, preferably smaller than 19 gauge, more preferably 23 gauge (or most preferably even 27 gauge) needle by manual pressure. In a particularly preferred embodiment, the low viscosity mixture should be a mixture capable of passing through a standard sterile filtration membrane such as a 0.22 μm syringe filter. A typical range of suitable viscosities would be, for example, 0.1 to 5000 mPas, preferably 1 to 1000 mPas, more preferably 10 to 750 mPas and most preferably 25 to 500 mPas at 20° C.

It has been observed that by the addition of small amounts of low viscosity organic mono-alcoholic solvent, as indicated herein, a very significant change in viscosity can be provided. For example, the addition of only 5% solvent to a lipid mixture can reduce viscosity 100-fold and addition of 10% may reduce the viscosity up to 10,000 fold. In order to achieve this non-linear, synergistic effect in lowering viscosity it is important that a solvent of appropriately low viscosity and suitable polarity be employed. Such solvents include those described herein infra. Preferred low-viscosity mixtures include molecular solutions, including dispersions of the peptide somatostatin receptor agonist in a molecular solution of the other components.

Upon administration, the preferred lipid-based pre-formulations of the present invention undergo a phase structure transition from a low viscosity mixture to a high viscosity (generally tissue adherent) depot composition. Generally this will be a transition from a molecular mixture, swollen $L_2$ and/or $L_3$ phase to one or more (high viscosity) liquid crystalline phases such as reversed hexagonal or cubic liquid crystalline phases or mixtures thereof. Further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. from 1 second up to 30 minutes, preferably up to 10 minutes, more preferably 5 minutes of less). The remainder of the composition may change phase to a liquid crystalline phase more slowly by diffusion and/or as the surface region disperses.

Without being bound by theory, it is believed that upon exposure to excess aqueous fluid, the pre-formulations of the invention lose some or all of the organic solvent included therein (e.g. by diffusion) and take in aqueous fluid from the bodily environment (e.g. the in vivo environment). For lipid pre-formulations, at least a part of the formulation preferably generates a non-lamellar, particularly liquid crystalline phase structure. In most cases these non-lamellar structures are highly viscous and are not easily dissolved or dispersed into the in vivo environment. The result is a monolithic "depot" generated in vivo with only a limited area of exposure to body fluids. Furthermore, because the non-lamellar structure has large polar, apolar and boundary regions, the lipid depot is highly effective in solubilising and stabilising active agents such as peptides and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively short biological half-life (see above).

By incorporation of at least 5% (e.g. at least 10%) of a polar solvent (especially at least 5% water and/or PG) into the pre-formulations, it is believed that the rate of phase transition to a non-lamellar (e.g. liquid crystalline) phase at the surface of the injected pre-formulation can be enhanced in comparison with compositions containing organic solvents in the substantial absence of water. The performance of the resulting depot is thus improved and further control over the release of active agent achieved.

The depot systems formed by the formulations of the present invention are highly effective in protecting the active agent from degradation and thus allow an extended release period. The formulations of the invention thus may provide in vivo depots of peptide somatostatin receptor agonists which require administration only once every 5 to 90 days preferably 5 to 60 days, more preferably 6 to 32. Evidently, a longer stable release period is desirable for patient comfort and compliance, as well as demanding less time from health professionals if the composition is not to be self-administered. Where the composition is to be self-administered, patient compliance may be aided by a weekly (e.g. every 7 days, optionally ±1 day) or monthly (e.g. every 28 or 30 days (optionally ±7 days) administration so that the need to administer is not forgotten.

A considerable advantage of the depot precursors of the present invention is that they are stable homogeneous phases. That is to say, they may be stored for considerable periods (preferably at least 6 months) at room or refrigerator temperature, without phase separation. As well as providing advantageous storage and facile administration, this allows for the dose of peptide somatostatin receptor agonist (e.g. pasireotide) to be selected by reference to the species, age, sex, weight, and/or physical condition of the individual subject, by means of injecting a selected volume.

The present invention thus provides for methods comprising the selection of a dosing amount specific to an individual, particularly by subject weight. The means for this dose selection is the choice of administration volume.

In one preferred aspect, the present invention provides a pre-formulation comprising components a), b), c), d), f) and at least one peptide somatostatin receptor agonist comprising pasireotide as indicated herein. The amounts of these components will typically be in the range 30-60% a), 30-70% b), 5-20% c) and 1-20% d), with the peptide somatostatin receptor agonist comprising pasireotide present at 0.01% to 10%, (such as 36-44% a), 36-44% b), 3-18% c) and 5-18% d) (preferably including at least 2% water), with the peptide somatostatin receptor agonist comprising pasireotide present at 1% to 8%), wherein the ratio of a:b is in the range 40:60 to 54:46.

Typically, component f) is present at an antioxidant to peptide somatostatin receptor agonist molar ratio of 1:50 to 1:6000, preferably 1:100 to 1:1300, and most preferably 1:150 to 1:1250. Since typical antioxidants are of lower molecular weight than peptide somatostatin receptor agonist (e.g. somatostatin analogue, e.g. octreotide), the proportion by weight of antioxidant may be relatively small. For example, with a small molecular weight antioxidant (e.g. less than 500 amu), 0.001 to 5% of the composition may be antioxidant, preferably 0.002 to 2%, more preferably 0.002 to 0.15%, e.g. 0.002 to 0.015%.

The pre-formulations of the present invention are highly advantageous in that they are stable to prolonged storage in their final "administration ready" form. As a result, they may readily be supplied for administration either by health professionals or by patients or their careers, who need not be fully trained health professionals and may not have the experience or skills to make up complex preparations. This is particularly important in long-duration, slow-effecting diseases such as diabetes.

The pre-formulation of the invention will preferably exclude any GLP-1, GLP-1 analogues and GLP-1 receptor agonists and/or antagonists. The pre-formulations of the invention will preferably exclude the following pre-formulations:

| Formulation | GLP-1/ wt % | PC/wt % | GDO3/ wt % | EtOH/ wt % | H₂O/wt % |
| --- | --- | --- | --- | --- | --- |
| Excl-K | 0.5 | 35.775 | 43.725 | 10 | 10 |
| Excl-L | 1.0 | 35.55 | 43.45 | 10 | 10 |
| Excl-M | 2.0 | 37.35 | 45.65 | 5 | 10 |
| Excl-N | 2.0 | 32.85 | 40.15 | 10 | 15 |
| Excl-O | 2.0 | 30.4 | 45.6 | 10 | 12 |
| Excl-P | 3.0 | 30 | 45 | 10 | 12 |
| Excl-Q | 3.0 | 31.875 | 43.125 | 10 | 12 |
| Excl-R | 3.0 | 32.4 | 39.6 | 10 | 15 |
| Excl-T | 2.0* | 32.85 | 40.15 | 10 | 15 |
| Excl-U | 2.0* | 30.4 | 45.6 | 10 | 12 | where EtOH is ethanol, PC is LIPOID S100 soybean phosphatidylcholine or LIPOID E 80 egg phosphatidylcholine (marked with *) and GDO is glycerol dioleate having quality (according to AC) as follows:

| GDO quality (according to AC) | Monoglycerides | Diglycerides | Triglycerides |
| --- | --- | --- | --- |
| GDO3 | 0.5% | 95.3% | 4.0% |

Devices

In a yet further aspect, the present invention provides a disposable administration device (which is also to include a device component) pre-loaded with a measured dose of a pre-formulation of the present invention. Such a device will typically contain a single dose ready for administration, and will generally be sterile-packed such that the composition is stored within the device until administration. Suitable devices include cartridges, ampoules and particularly syringes and syringe barrels, either with integral needles or with standard (e.g. luer) fittings adapted to take a suitable disposable needle. Similarly appropriate devices include a needle-less injector, a multi- or single-use autoinjector combined with a pre-filled syringe, a cartridge, optionally combined with a multi-use pen device, or a vial. Evidently, such pre-filled syringes and cartridges may be for any appropriate injecting device, such as a multi-use or single-use injector or needle-less injection unit.

The devices of the invention may preferably contain the pre-formulation of the invention which delivers a dosage in the range of 5 to 150 mg/ml, preferably 10 to 100 mg/ml, most preferably 10 to 70 or 10 to 90 mg/ml, for example 20 to 60 or 20 to 80 mg/ml, such as 20 to 60 or 30 to 60 mg/ml.

In one embodiment applicable to all aspects of the invention, the devices of the invention may contain a single dose of 1 to 200 mg, for example 1 to 150 mg (e.g. 1 to 120 mg) of peptide somatostatin receptor agonist comprising pasireotide, preferably pasireotide pamoate.

The devices of the invention may contain peptide somatostatin receptor agonist comprising pasireotide, preferably pasireotide pamoate, at around 0.1 to 6 mg (e.g. 0.2 to 4 mg) per day between scheduled administrations, for example around 0.6 (e.g. 0.6 to 3) mg per day, particularly 1 to 2 mg/day.

The devices of the invention may contain a total volume for administration of no more than 5 ml, for example no more than 2 ml, such as approximately 1.5 ml.

The pre-filled devices of the invention may also suitably be included in an administration kit, which kit also forms a further aspect of the invention. In a still further aspect, the invention thus provides a kit for the administration of at least one peptide somatostatin receptor agonist comprising pasireotide, said kit containing a measured dose of a formulation of the invention and optionally an administration device or component thereof. Preferably the dose will be held within the device or component, which will be suitable for i.m. or preferably s.c. administration. The kits may include additional administration components such as needles, swabs, etc. and will optionally and preferably contain instructions for administration. Such instructions will typically relate to administration by a route as described herein and/or for the treatment of a disease indicated herein above.

Kits

The invention provides for a pre-filled administration device as indicated herein and a kit as indicated herein comprising a pre-formulation as described herein.

In an alternative aspect of the present invention, the "kit" may contain at least two vessels, a first containing a low viscosity mixture of components a) to d), as described here, and a second containing a measured dose of at least one peptide somatostatin receptor agonist comprising pasireotide as described herein. The antioxidant component f) may be formulated with the active agent, or more preferably as part of the low viscosity mixture, which will then comprise components a) to d) and f).

Such a "two component kit" may comprise the peptide somatostatin receptor agonist as a powder formulation in one vial or pre-filled syringe and components a) to d) (and optionally f)) in a second vial or pre-filled syringe. In the case of two syringes, before injection, the pre-filled syringes are connected and the powder comprising active agent is mixed with the matrix formulation by moving the syringe barrels back and forth, forming a solution or suspension which is injected. Alternatively, the liquid lipid formulation is drawn from one vial, or is pre-filled into a syringe, and is injected into a vial containing peptide powder. This formulation may subsequently be mixed by hand shaking or other suitable reconstitution method (e.g. vortex mixing etc.). The solvent component may be present in either or both vessels (e.g. vials or syringes). Where the solvent is at least partially constituted with the active agent, this will generally be in the form of a solution or suspension.

In this aspect, the invention therefore provides a two component kit comprising i) a first vessel containing a low viscosity mixture of components a) to d) as described herein;

ii) a second vessel containing at least one peptide somatostatin receptor agonist comprising pasireotide, iii) an antioxidant component f) optionally in a third vessel, preferably in the second vessel, or most preferably in the first vessel;

iv) optionally and preferably at least one of:
1) at least one syringe (which may be one or both of said first and second vessels);
2) a needle for administration, such as those described herein;
3) instructions for generation of a composition of the invention from the contents of the first and second vessels;
4) instructions for administration, whereby to form a depot as described herein.

Preferred Features and Combinations

In combination with the features and preferred features indicated herein, the pre-formulations of the invention may have one or more of the following preferred features independently or in combination:

All proportions indicated herein may optionally be varied by up to 10% of the amount specified, optionally and preferably by up to 5%;

Component a) comprises, consists essentially of or preferably consists of GDO;

Component b) comprises, consists essentially of or preferably consists of soy PC and/or "high purity PC" such as DOPC;

Component c) comprises, consists essentially of or preferably consists of a 1, 2, 3 or 4 carbon alcohol, preferably isopropanol or more preferably ethanol;

Component d) comprises, consists essentially of or preferably consists of a polar solvent such as water, propylene glycol, or mixtures thereof;

Component f) comprises, consists essentially of or preferably consists of ascorbic acid, ascorbyl palmitate, ethylenediaminetetraacetic acid (EDTA), and/or citric acid;

The pre-formulation contains at least one peptide somatostatin receptor agonist comprising pasireotide, preferably pasireotide pamoate;

The pre-formulation has a low viscosity as indicated herein.

The pre-formulation comprises forms a liquid crystalline phase as indicated herein upon in vivo administration.

The pre-formulation generates a depot following in vivo administration, which depot releases at least one somatostatin receptor agonist at a therapeutic level over a period of at least 7 days, preferably at least 28 days, more preferably at least 60 days.

The pre-formulation has a higher loading of peptide somatostatin receptor agonist comprising pasireotide than is stable in the same formulation in the absence of component d)

The pre-formulation has a higher loading of peptide somatostatin receptor agonist comprising pasireotide than is obtainable by equilibration at 25° C. of the same formulation in the absence of component d).

In combination with the features and preferred features indicated herein, the method(s) of treatment of the present invention may have one or more of the following preferred features independently or in combination:

The method comprises the administration of at least one formulation with one or more preferred features as indicated above;

The method comprises the administration of at least one formulation as indicated herein by i.m., s.c. or preferably deep s.c. injection;

The method comprises administration by means of a pre-filled administration device as indicated herein;

The method comprises administration through a needle no larger than 20 gauge, preferably smaller than 20 gauge, and most preferably 23 gauge or smaller;

The method comprises a single administration every 20 to 100 days, preferably 28 to 60 days (for example 30-45 days).

In combination with the features and preferred features indicated herein, the use(s) of the pre-formulations indicated herein in the manufacture of medicaments may have one or more of the following preferred features independently or in combination:

The use comprises the use of at least one formulation with one or more preferred features as indicated above;

The use comprises the manufacture of a medicament for administration of at least one formulation as indicated herein by i.m., s.c. or preferably deep s.c. injection;

The use comprises the manufacture of a medicament for administration by means of a pre-filled administration device as indicated herein;

The use comprises the manufacture of a medicament for administration through a needle no larger than 20 gauge, preferably smaller than 20 gauge, and most preferably 23 gauge or smaller;

The use comprises the manufacture of a medicament for administration once every 20 to 100 days, preferably 28 to 60 days, more preferably 30 to 45 days.

In combination with the features and preferred features indicated herein, the pre-filled devices of the invention may have one or more of the following preferred features independently or in combination:

They contain a preferred formulation as indicated herein;
They comprise a needle smaller than 20 gauge, preferably no larger than 23 gauge;
They contain a single dose of 1 to 300 mg of peptide somatostatin receptor agonist comprising pasireotide, preferably 1 to 200 mg, more preferably 5-150 mg, for example 10-100 mg, most preferably 20-70 mg and especially preferably 30-60 mg.
They contain a homogeneous mixture of a composition of the invention in ready-to-inject form.
They contain a formulation of components a) to c) for combination with a peptide somatostatin receptor agonist comprising pasireotide whereby to form a pre-formulation of the invention.
They contain a peptide somatostatin receptor agonist comprising pasireotide for combination with a formulation of components a) to d) and optionally f), whereby to form a pre-formulation of the invention.
They contain a total volume for administration of no more than 5 ml, preferably no more than 3 ml, for example no more than 2 ml, more preferably no more than 1.5 ml.

In combination with the features and preferred features indicated herein, the kits of the invention may have one or more of the following preferred features independently or in combination:

They contain a preferred formulation as indicated herein;
They contain a pre-filled device as indicated herein; They contain a needle smaller than 20 gauge, preferably no larger than 23 gauge;
They contain a single dose of 1 to 300 mg of peptide somatostatin receptor agonist comprising pasireotide, preferably 1 to 200 mg, more preferably 5-150 mg, for example 10-100 mg, most preferably 20-70 mg and especially preferably 30-60 mg;
They contain a "two compartment kit" comprising at least two vessels containing a lipid formulation of the invention and a peptide somatostatin receptor agonist comprising pasireotide powder, respectively.
They contain a total volume for administration of no more than 5 ml, preferably no more than 3 ml, for example no more than 2 ml, more preferably no more than 1.5 ml.
They contain instructions for administration by a route and/or at a frequency as indicated herein;
They contain instructions for administration for use in a method of treatment as described herein.

The Invention will now be further illustrated by reference to the following non-limiting Examples and the attached Figures.

EXAMPLES

Materials
SPC Soy phosphatidylcholine (Lipid S 100)—Lipoid
GDO Glycerol dioleate (Rylo DG19 Pharma)—Danisco
DOPC Dioleoyl phosphatidylcholine—NOF
EtOH Ethanol—Solveco
PG Propylene glycol—Fischer
WFI Water for injection—Apoteket
EDTA Ethylenediaminetetraacetic acid, disodium salt—Sigma Aldrich
SOM230(Pm) SOM230 pamoate (Pasireotide pamoate)—Novartis Pharma
SOM230(Ac) SOM230 acetate (Pasireotide acetate)—Novartis Pharma Example 1: Solubility Screening Placebo lipid mixture formulations as well as formulations of the single respective lipid alone were prepared in 1 OR vials according to Table 1. The sample size was 6 g. Samples of SOM230 (pasireotide pamoate) of the respective formulation type with a drug load of 3 wt % (corrected for peptide purity and content) were prepared in 2R vials, except for Formulation type 15 where only 1 wt % 5230 was evaluated. The samples were allowed to equilibrate at ambient room temperature; samples with formulation types 1-8 on end-over-end rotation and samples with formulation types 9-12 on magnetic stirring. The flow chart in FIG. 1 describes the sample preparation process. The screening covered the following formulation variables:

Lipid weight ratio (SPC/GDO weight ratio)
Co-solvent nature and concentration
Single lipid formulations
Single solvent (only PG)

TABLE 1

Compositions of placebo lipid formulations (wt %) used for solubility screening.

| Formulation type | SPC | GDO | EtOH | PG | WFI | Comment |
|---|---|---|---|---|---|---|
| 1 | 47.5 | 47.5 | 5 | — | — | SPC/GDO = 50/50 wt/wt |
| 2 | 38 | 57 | 5 | — | — | SPC/GDO = 40/60 wt/wt |
| 3 | 57 | 38 | 5 | — | — | SPC/GDO = 60/40 wt/wt |
| 4 | 45 | 45 | 10 | — | — | 10 wt % EtOH |
| 5 | 42.5 | 42.5 | 15 | — | — | 15 wt % EtOH |
| 6 | 45 | 45 | 5 | 5 | — | 5 wt % PG |
| 7 | 42.5 | 42.5 | 5 | 10 | — | 10 wt % PG |
| 8 | 40 | 40 | 5 | 15 | — | 15 wt % PG |
| 9 | 42.5 | 42.5 | 7.5 | 7.5 | — | 1/1 EtOH/PG; Magnetic stirring |
| 10 | 40 | 40 | 10 | 10 | — | 1/1 EtOH/PG; Magnetic stirring |
| 11 | 40 | 40 | 10 | — | 10 | 1/1 EtOH/WFI; Magnetic stirring |
| 12 | 35 | 35 | 15 | — | 15 | 1/1 EtOH/WFI; Magnetic stirring |
| 13 | 78 | — | 11 | 11 | — | Single lipid (SPC) |
| 14 | — | 78 | 11 | 11 | — | Single lipid (GDO) |
| 15 | — | — | — | 100 | — | PG only |

The samples were studied by visual inspection and the appearance was noted. Additional SOM230 drug powder in steps of 1 wt % (corrected for peptide purity and content according to CoA) was added to any homogenous and transparent sample with the exception of Formulation type 15. Mixing at ambient room temperature and visual observation continued after addition of more SOM230 drug powder.

The results of the solubility screening are summarized in Table 2. It is concluded that a dose strength of up to at least 10 wt % or approximately 100 mg SOM230 free base/mL is attainable for some formulation types. Furthermore, PG appears to be a relatively good solvent for SOM230 (>1 wt %) in comparison to the poor solubility in EtOH (<<1 wt %).

Higher drug loads of SOM230, up to 10 wt % (or approximately 100 mg/mL (corrected)), were achieved using a co-solvent combination of EtOH/PG at concentrations of 10 wt % each. Formulations comprising EtOH only as co-solvent were not as effective as the combination of EtOH/PG or EtOH/WFI for SOM230 loading. Formulations comprising only the single respective lipid excipient (Formulation types 13 and 14) displayed lower drug loading capability (<3 wt %) compared to lipid mixtures with equivalent solvent composition indicating strong synergistic solubility enhancing effects by combining the components of the formulation of the invention.

TABLE 2

Results of the solubility screening. For formulation compositions, see Table 1.

| Formulation type | Maximum concentration evaluated (wt %) | Maximum SOM230 drug load (wt %) Highest concentration observed with transparent and homogenous sample (wt %)/Comment |
|---|---|---|
| 1 | 3 | Some non-dissolved material in the bottom of the vial remained |
| 2 | 3 | Small amount of non-dissolved material remained |
| 3 | 3 | Small amount of non-dissolved material remained |
| 4 | 4 | 3 |
| 5 | 5 | 4 (a few non-dissolved particles/crystals remained at 5 wt %) |
| 6 | 5 | 4 |
| 7 | 4 | 3 (one single remaining particle at 4 wt %) |
| 8 | 5 | 5 |
| 9 | 6 | 6 |
| 10 | 10 | 10 |
| 11 | 10 | 6 (some non-dissolved material remained at 10 wt %) |
| 12 | 4 | 3 (opalescent sample at 4 wt %) |
| 13 | 3 | Turbid/opalascent and non-dissolved material remained at 3 wt % |
| 14 | 3 | Turbid/opalascent, oil-like drops and non-dissolved material remained at 3 wt % |
| 15 | 1 | 1 |

The solubility screening results are summarized as follows:
- Multiple formulation types were found to allow for drug load levels of 30-60 mg/mL
- Increased co-solvent levels and combination of EtOH and PG or EtOH and water increased SOM230 solubility
- A drug load of (at least) 10 wt % (ca 100 mg/mL) was verified for at least one formulation variant
- The combination of SPC and GDO increased SOM230 solubility in a synergistic way compared with the single lipid mixtures
- PG appeared to be a relatively good solvent for SOM230

Example 2—Injectability, Density and Viscosity

Formulations according to Table 3 were prepared and used for evaluation of injectability, density and viscosity. The lipid/SOM230 formulations with drug loads of 3 and 6 wt %, respectively, were prepared in 15R injection glass vials.

TABLE 3

Compositions of lipid/SOM230 formulations (wt %).

| Sample ID | SOM230* | SPC | DOPC | GDO | EtOH | PG | WFI |
|---|---|---|---|---|---|---|---|
| 4071S230-1201-60 | 4.31 | 40.3 | — | 40.4 | 7.5 | 7.5 | — |
| 4071S230-1201-61 | 4.31 | 37.8 | — | 37.8 | 10.0 | 10.0 | — |
| 4071S230-1201-62 | 4.31 | 37.8 | — | 37.8 | 10.1 | — | 10.0 |
| 4071S230-1201-63 | 8.54 | 38.2 | — | 38.2 | 7.5 | 7.5 | — |
| 4071S230-1201-64 | 8.61 | 35.7 | — | 35.7 | 10.0 | 10.0 | — |
| 4071S230-1201-65 | 8.64 | 35.6 | — | 35.7 | 10.0 | — | 10.0 |
| 4071S230-1204-82 | 8.60 | 34.7 | — | 34.7 | 12.0 | — | 10.0 |
| 4071S230-1204-83 | 8.60 | 33.2 | — | 33.2 | 15.0 | — | 10.1 |
| B4071S230-1206-09 | 5.91 | 39.55 | — | 39.55 | 7.50 | 7.50 | — |
| B4071S230-1206-10 | 7.39 | 38.81 | — | 38.81 | 7.50 | 7.50 | — |
| B4071S230-1206-11 | 5.91 | — | 39.55 | 39.55 | 7.50 | 7.50 | — |
| B4071S230-1206-12 | 5.91 | 39.55 | — | 39.55 | 10.00 | 5.00 | — |

*Pamoate salt; 4.3, 5.9, 7.4 and 8.6 wt % SOM230 pamoate salt corresponds to ca 30, 40, 50 and 60 mg SOM230 free base/g, respectively, when corrected for peptide purity and content.

The preparation procedure of the samples was as described in FIG. 1. A magnetic stirring bar was added to the samples (sample size 6 g) followed by magnetic stirring at ambient room temperature. The samples were studied by visual inspection and the approximate time to complete dissolution was noted.

The formulations with 30 mg/g were transparent and homogenous within 48 h. The samples with 60 mg/g were homogenous and transparent within 3 days. No special efforts (such as increasing the stirring rate) were made to speed up dissolution times for these preparations.

Injectability (Flow Rates)

The injectability or flow rate of each formulation was evaluated according to the following method: a constant force is applied to the selected syringe configuration filled with the respective formulation. The injection is then performed at ambient room temperature into an empty vial and the weight of the injected formulation is noted and the time to complete the injection is measured. The injection volume per injection test was approx. 0.4-0.6 mL and duplicate tests were performed. The constant force applied was 20 N. The syringe and needle format used for the injectability tests are given in Table 4.

TABLE 4

Syringe and needle configuration.

| Syringe | Supplied by | Needle | Supplied by |
|---|---|---|---|
| 1 mL long glass Luer-Lock | Gerresheimer | 23G thin-wall (tw), 16 mm | Terumo |

Stoppers used were from West (4432/50 grey B240 Westar®) with plunger rod 55103 supplied by Fresenius Kabi (FKA).

Injectability results are summarized in FIG. 2. The injectability is given as seconds per mL (inverse of the flow rate). The values were converted from seconds per gram to seconds per mL by the use of formulation density values (see below). The time for injection, using the 20 N constant force, varied between approximately 8-30 seconds depending on formulation.

Density

The density of each formulation was determined using an Anton Paar density meter DMA 4500 M (1360) at 20° C. Single tests were performed on each formulation. The results are presented in Table 5.

TABLE 5

Density measurements on lipid/SOM230 formulations. Formulation compositions are provided in Table 3.

| Sample ID | Density (g/mL) |
|---|---|
| 4071S230-1201-60 | 0.967 |
| 4071S230-1201-61 | 0.963 |
| 4071S230-1201-62 | 0.964 |
| 4071S230-1201-63 | 0.979 |
| 4071S230-1201-64 | 0.975 |
| 4071S230-1201-65 | 0.976 |
| 4071S230-1204-82 | 0.973 |
| 4071S230-1204-83 | 0.967 |
| B4071S230-1206-09 | 0.971 |
| B4071S230-1206-10 | 0.975 |
| B4071S230-1206-11 | 0.969 |
| B4071S230-1206-12 | 0.965 |

Viscosity

The viscosity was measured using a Bohlin Visco 88 BV instrument (rotating inner cylinder, stationary outer cylinder) at three speed settings (three shear rates). Single tests were performed for each formulation.

The measurements were performed at room temperature (ambient). The results are shown in Table 6 as mean viscosity for the different speed settings. No difference in viscosity values (within experimental variation) could be observed between the different shear rates indicating Newtonian behaviour.

TABLE 6

Viscosity measurements on lipid/SOM230 formulations. Formulation compositions are provided in Table 3.

| Sample ID | Viscosity (mPas) |
|---|---|
| 4071S230-1201-60 | 308 |
| 4071S230-1201-61 | 168 |
| 4071S230-1201-62 | 364 |
| 4071S230-1201-63 | 599 |
| 4071S230-1201-64 | 307 |
| 4071S230-1201-65 | 425 |
| 4071S230-1204-82 | 284 |
| 4071S230-1204-83 | 142 |

It may be noted that by doubling the SOM230 drug load from ca 30 to 60 mg/mL, the viscosity almost doubled for formulations with EtOH/PG whereas the viscosity increase for the corresponding EtOH/WFI formulations was only about 20%. The link between injectability and viscosity is illustrated in FIG. 3. As expected for these types of formulations, the injectability (calculated as time for 1 mL injection) is close to linearly proportional to viscosity.

Example 3—Comparative Formulation Studies with SOM230 Acetate and SOM230 Hydrochloride Preparation of SOM230 Hydrochloride The SOM230 hydrochloride salt was prepared from SOM230 acetate using an ion exchange process. The ion exchange column was prepared by putting glass wool (HPLC grade) in the bottom of a 200 mL glass chromatography column from Sigma-Aldrich. A mixture of approximately 20 mL of Dowex 1×2 chloride form (Sigma-Aldrich) and distilled water (volume ratio 1:1) was added followed by a piece of glass wool on the top of the column. The column was rinsed with distilled water and the conductivity was measured. When the conductivity was below 35 µS/cm, a volume of 40 mL WFI was added to the column.

For the ion exchange, a SOM230 acetate (SOM230(Ac)) sample was prepared in a 100 mL Pyrex flask. The sample was diluted with WFI to a final volume of 65.55 mL and a concentration of 3.8 mg SOM230(Ac)/mL. The SOM230 (Ac) solution was transferred to the ion exchange column using a plastic disposable pipette. The Pyrex flask was rinsed with an additional 20 mL of WFI which was also transferred to the column. Sample fractions of 20 mL were collected as the column was rinsed with WFI. The conductivity was measured in each fraction and fractions were collected until the conductivity was below 75 µS/cm. All fractions were pooled together in a 1000 mL round bottom flask (pooled volume ca 180 mL).

The round bottom flask from the previous step was kept at 2-8° C. until further use. The flask was mounted on a Rotavapor and put on approximately 80% of maximum rotation speed. The solution was shell-frozen by lowering the rotating flask in an EtOH bath containing dry ice and a mixture of 99.5% and 96% EtOH (volume ratio 1:1) for 10 minutes. After shell-freezing, the round bottom flask was kept at −80° C. for 30 min before the freeze-drying was started.

The material was freeze-dried for almost 30 h. The SOM230 hydrochloride (SOM230(Cl)) powder obtained was thereafter transferred and weighed into a 250 mL Pyrex flask. The total amount of SOM230(Cl) recovered was 0.215 g, resulting in a 86% yield of the ion exchange process. The peptide powder was stored in a freezer (<−15° C.) until further use.

Pharmaceutical Analysis of SOM230 Hydrochloride

A comparison of the purity data (HPLC) for the SOM230 (Ac) and the SOM230(Cl) indicated that the integrity of the SOM230 material remained intact through the ion exchange process. The chloride content was determined by HPLC to 5.15 wt % which corresponded well to the determined acetate content of 8.90 wt % in the original SOM230(Ac) drug powder when the acetate/chloride weight ratio is taken into account. The analysis of the SOM230(Cl) drug powder did not detect any presence of acetate ions, demonstrating a successful and complete ion exchange process.

Solubility

Lipid formulations with SOM230(Ac) and SOM230(Cl), respectively, were prepared as described in Example 1 according to Tables 8 and 9. The target concentration was a SOM230 (free base) concentration of approximately 30 mg/mL.

TABLE 8

Compositions (wt %) of lipid/SOM230(Ac) formulations.

| Sample ID | SOM230(Ac) | SPC | GDO | EtOH | PG | WFI |
|---|---|---|---|---|---|---|
| 4071S230(Ac)-1203-120 | 3.75 | 43.1 | 43.1 | 10.0 | — | — |
| 4071S230(Ac)-1203-121 | 3.79 | 40.6 | 40.6 | 7.5 | 7.5 | — |
| 4071S230(Ac)-1203-122 | 3.75 | 38.0 | 38.0 | 10.0 | 10.0 | — |
| 4071S230(Ac)-1203-123 | 3.77 | 38.1 | 38.1 | 10.0 | — | 10.0 |

TABLE 9

Compositions (wt %) of lipid/SOM230(Cl) formulations.

| Sample ID | SOM230(Cl) | SPC | GDO | EtOH | PG | WFI |
|---|---|---|---|---|---|---|
| 4071S230(Cl)-1203-124 | 3.82 | 43.1 | 43.1 | 10.0 | — | — |
| 4071S230(Cl)-1203-125 | 3.69 | 40.6 | 40.6 | 7.5 | 7.5 | — |
| 4071S230(Cl)-1203-126 | 3.72 | 38.0 | 38.0 | 10.0 | 10.0 | — |
| 4071S230(Cl)-1203-127 | 3.84 | 38.1 | 38.1 | 10.0 | — | 10.0 |

The samples were allowed to equilibrate at room temperature on a magnetic stirrer (500 rpm) after brief vortex mixing. Visual inspection was performed after 1.5 and 24 hours. All formulations indicated in Tables 8 and 9 were transparent and homogenous after 24 h mixing indicating good solubility of both the acetate and the hydrochloride salt forms. Formulations of SOM230 pamoate (SOM230(Pm)) with identical lipid and co-solvent composition to those described in Tables 8 and 9 were prepared according to the same procedure.

Stability Comparison

The lipid/SOM230(Pm), lipid/SOM230(Cl) and lipid/SOM230(Ac) formulations were divided into two 2R vials which were placed at 60° C. and the remaining amount from the preparation was assayed by HPLC (time point zero).

The samples stored at 60° C. were pulled out after 2 weeks of storage for visual inspection and HPLC analysis.

The results of the HPLC analysis are provided in FIG. 4 and shows the difference in stability profile between the salt forms for the investigated formulation variants (because the SPC/GDO weight ratio was equivalent for all salt forms, formulation variants are differentiated by their solvent composition in FIG. 4). The results after storage for 2 weeks at 60° C. clearly indicate that SOM230 pamoate is the most stable salt form in the lipid formulations. The hydrochloride salt of SOM230 was also more stable than the acetate salt but not as stable as the pamoate salt.

Example 4—In Vivo PK Studies I and II

Formulations

Formulations used for in vivo pharmacokinetic (PK) study I in rat (study no. PK-12-437) are outlined in Table 10. A constant SOM230 load (pamoate salt) corresponding to 30 mg SOM230 free base/mL was selected for all formulations. Combinations of different solvents, EtOH, EtOH/PG and EtOH/WFI, were investigated. The primary aim was to characterize the PK profiles of the different formulation variants of SOM230 pamoate.

TABLE 10

Lipid/SOM230 formulations selected for PK study I (PK-12-437). Compositions are provided in wt %.

| Batch no. | Test item | SOM230 (pamoate)* | GDO | SPC | EtOH | PG | WFI |
|---|---|---|---|---|---|---|---|
| B4071S230-1202-01 | 4071S230-A | 4.45 | 40.28 | 40.28 | 7.50 | 7.50 | — |
| B4071S230-1202-02 | 4071S230-B | 4.47 | 37.77 | 37.77 | 10.00 | 10.00 | — |
| B4071S230-1202-03 | 4071S230-C | 4.46 | 37.77 | 37.77 | 10.00 | — | 10.00 |
| B4071S230-1202-04 | 4071S230-D | 4.48 | 42.76 | 42.76 | 10.00 | — | — |

*The SOM230 pamoate concentration corresponds to 30 mg SOM230 free base/mL when corrected for peptide purity and content and formulation density.

Formulations used for in vivo PK study II in rat (study no. PK-12-438) are outlined in Table 11. The primary aim was to characterize effects of increasing the SOM230 load on the PK profile. For this study a combination of EtOH and water (WFI) was used as solvent for the formulations at a fixed concentration of 10 wt % of each component as indicated in Table 11. Formulation 4071 S230-C was investigated in both PK studies providing a bridge between the studies.

TABLE 11

Lipid/SOM230 formulations selected for PK study II (PK-12-438). Compositions are provided in wt %.

| Batch no. | Test item | S230 (pamoate)* | GDO | SPC | EtOH | WFI |
|---|---|---|---|---|---|---|
| B4071S230-1202-05 | 4071S230-C | 4.46 | 37.77 | 37.77 | 10.00 | 10.00 |
| B4071S230-1202-06 | 4071S230-E | 5.91 | 37.05 | 37.05 | 10.00 | 10.00 |
| B4071S230-1202-07 | 4071S230-F | 7.39 | 36.31 | 36.31 | 10.00 | 10.00 |
| B4071S230-1202-08 | 4071S230-G | 8.81 | 35.60 | 35.60 | 10.00 | 10.00 |

*The SOM230 pamoate concentrations correspond to 30, 40, 50 and 60 mg SOM230 free base/mL, respectively, when corrected for peptide purity and content and formulation density.

Manufacturing of the formulations in Tables 10 and 11 was performed essentially as described in Example 1 with the addition of a sterile filtration step after complete mixing into homogenous liquid formulations. The formulations were sterile filtered under 2.5 bar nitrogen pressure using a PVDF 0.2 micron membrane filter from Millipore.

In Vivo Study Performance

The formulations in Table 10 (PK-12-437) were injected subcutaneously to male Sprague-Dawley rats (body weight ca 330 g) at a dose volume of 0.2 mL per animal (6 mg SOM230/animal) whereas the formulations in Table 11 (PK-12-438) were injected at a dose volume of 0.1 mL/animal corresponding to 3, 4, 5 and 6 mg SOM230/animal for 4071S230-C, 4071S230-E, 4071S230-F and 4071S230-G, respectively. Blood for pharmacokinetics were collected pre-dose, and 1 hour, 6 hours, 1 day, 7 days, 14 days, 21 days, 28 days and 35 days after dosing. Blood samples of 0.5 mL were collected by sub-lingual bleeding into EDTA-treated test tubes (Capiject 3T-MQK, Terumo Medical Corporation). The blood was placed on ice immediately after collection and centrifuged (approximately 1500×g, at 5° C. for 10 min) within 30 to 60 minutes. The plasma was transferred into properly labelled translucent 1.5-mL propylene test tubes (Microcentrifuge tubes, Plastibrand, Buch & Holm) and stored below −70° C. until bioanalysis by ELISA assay.

Pharmacokinetics

The PK profiles of the respective formulations in Tables 10 and 11 are provided in FIGS. 5 and 6.

As is clear from the data in FIG. 5, the PK profiles are very flat with Cmax/C28d plasma concentration ratios between about 3.1-4.9, where Cmax is the maximum concentration observed and C28d is the plasma concentration observed at 28 days post injection. In terms of Cmax/Caverage ratios, where Caverage is the average plasma concentration over the target 28 days duration, this ratio is even lower than the respective Cmax/C28d ratio. Thus, the initial release (or burst) is low followed by consistent plasma levels, fulfilling the PK requirements for effective depot formulations. The main PK-parameters obtained in PK-12-437 are tabulated in Table 12.

TABLE 12

PK parameters obtained in PK study no. PK-12-437. Formulation compositions are provided in Table 10.

| Test item | Dose (mg) | Cmax (ng/mL) | C28d (ng/mL) | Cmax/C28d | AUClast (ng/mL * d) |
|---|---|---|---|---|---|
| 4071S230-A | 6.0 | 187.7 ± 54.2 | 65.3 ± 34.2 | 3.4 | 3364 ± 806 |
| 4071S230-B | 6.0 | 288.2 ± 98.2 | 70.2 ± 28.4 | 4.9 | 4550 ± 891 |
| 4071S230-C | 6.0 | 190.2 ± 49.5 | 63.3 ± 13.1 | 3.1 | 3421 ± 852 |
| 4071S230-D | 6.0 | 150.7 ± 28.1 | 53 ± 24.1 | 3.4 | 2662 ± 864 |

The data in FIG. 6 show again that the release rate is consistent over time resulting in very flat PK profiles. Cmax/C28d plasma concentration ratios were between about 3.4-9.2 for the formulations indicated in Table 11. In terms of Cmax/Caverage ratios, this ratio is even lower than the respective Cmax/C28d ratio. The main PK-parameters obtained in PK-12-438 are tabulated in Table 13.

TABLE 13

PK parameters obtained in PK study no. PK-12-438. Formulation compositions are provided in Table 11.

| Test item | Dose (mg) | Cmax (ng/mL) | C28d (ng/mL) | Cmax/C28d | AUClast (ng/mL * d) |
|---|---|---|---|---|---|
| 4071S230-C | 3.0 | 104.8 ± 39.8 | 29.2 ± 6.6 | 3.8 | 1893 ± 568 |
| 4071S230-E | 4.0 | 185.3 ± 80.9 | 56.0 ± 7.4 | 3.4 | 2707 ± 918 |
| 4071S230-F | 5.0 | 311 ± 88.9 | 103.9 ± 59.1 | 4.1 | 4649 ± 505 |
| 4071S230-G | 6.0 | 481.2 ± 100.3 | 53.2 ± 14.8 | 9.2 | 5742 ± 1021 |

Dose linearity with respect to exposure (AUC) was clearly indicated as shown in FIG. 7 ($R^2=0.977$). Dose linearity with respect to Cmax was also shown as indicated in FIG. 8 ($R^2=0.975$).

Example 5—Explorative Stability Testing

The formulations evaluated in the PK studies (Tables 10 and 11) were also subjected to explorative stability testing. In addition to these formulations, one additional formulation was manufactured comprising the antioxidant disodium ethylenediamine tetraacetic acid (EDTA). The formulation composition of the additional formulation is provided in Table 14 (see Tables 10 and 11 for compositions of the other formulations).

TABLE 14

Lipid/SOM230 formulation comprising antioxidant included in the explorative stability testing. Composition in wt %.

| Batch/Sample no. | SOM230 (pamoate)* | GDO | SPC | EtOH | WFI/EDTA** |
|---|---|---|---|---|---|
| 4071S230-1202-109 | 4.46* | 37.77 | 37.77 | 10.00 | 10.00 |

*The SOM230 pamoate concentration corresponds to 30 mg SOM230 free base/mL when corrected for peptide purity and content and formulation density.
**0.1 mg disodium EDTA/mL in WFI.

Summary of Explorative Stability Study Set-Up

Each formulation was filled in 2R vials with 0.8 g per vial followed by flushing with nitrogen for 5 seconds and closing with Teflon-coated rubber stoppers and aluminum crimp caps. The storage conditions for formulations provided in Tables 10 and 14 were 5° C., 25° C./60% RH, 40° C./75% RH and 60° C. whereas the formulations provided in Table 11 were only evaluated at 5° C. and 25° C./60% RH. The samples were always allowed to equilibrate for 60 min at ambient RT before start of the HPLC UV-DAD (diode array detection) analysis.

Results

The assayed (HPLC UV-DAD) peptide contents after up to 8 weeks of storage are summarized in Tables 15 and 16 whereas the peptide purity results, calculated as the area of the SOM230 peak divided by the total area of the SOM230 peak and related substances, are summarized in Tables 17 and 18.

TABLE 15

SOM230 content analysis (by HPLC UV-DAD) of formulations (see
Tables 10 and 14) stored at 5, 25, 40 and 60° C. up to 8 weeks.

| Batch/Sample no. | t = 0 SOM230 content (mg/g) | Storage conditions | t = 2 weeks SOM230 content (mg/g) | % of start value | t = 4 weeks SOM230 content (mg/g) | % of start value | t = 8 weeks SOM230 content (mg/g) | % of start value |
|---|---|---|---|---|---|---|---|---|
| B4071S230-1202-01 | 30.3 | 5° C. | — | — | 31.9 | 105.3 | 31.4 | 103.7 |
| | | 25° C./60% RH | — | — | 31.8 | 105.0 | 30.8 | 101.7 |
| | | 40° C./75% RH | 30.7 | 101.3 | 30.7 | 101.2 | 29.2 | 96.2 |
| | | 60° C. | 27.1 | 89.5 | 25.1 | 82.9 | — | — |
| B4071S230-1202-02 | 30.6 | 5° C. | — | — | 32.5 | 106.3 | 31.3 | 102.4 |
| | | 25° C./60% RH | — | — | 32.1 | 104.9 | 31.0 | 101.3 |
| | | 40° C./75% RH | 30.9 | 100.8 | 31.6 | 103.2 | 29.2 | 95.4 |
| | | 60° C. | 26.4 | 86.1 | 26.0 | 84.9 | — | — |
| B4071S230-1202-03 | 30.7 | 5° C. | — | — | 32.1 | 104.6 | 31.2 | 101.6 |
| | | 25° C./60% RH | — | — | 31.8 | 103.5 | 30.6 | 99.7 |
| | | 40° C./75% RH | 30.4 | 99.0 | 29.2 | 101.6 | 29.3 | 95.3 |
| | | 60° C. | 26.9 | 87.5 | 27.1 | 88.3 | — | — |
| B4071S230-1202-04 | 28.7 | 5° C. | — | — | 30.1 | 104.7 | 29.4 | 102.6 |
| | | 25° C./60% RH | — | — | 29.8 | 104.0 | 29.2 | 101.9 |
| | | 40° C./75% RH | 29.1 | 101.4 | 29.2 | 101.6 | 27.9 | 97.1 |
| | | 60° C. | 25.9 | 90.3 | 23.4 | 81.6 | — | — |
| 4071S230-1202-109 | 30.4 | 5° C. | — | — | 32.8 | 107.7 | 31.3 | 102.9 |
| | | 25° C./60% RH | — | — | 31.8 | 104.5 | 30.9 | 101.5 |
| | | 40° C./75% RH | 30.7 | 100.9 | 31.2 | 102.7 | 30.0 | 98.6 |
| | | 60° C. | 28.3 | 91.2 | 27.4 | 90.1 | — | — |

TABLE 16

SOM230 content analysis (by HPLC UV-DAD) of formulations
(see Table 11) stored at 5 and 25° C. up to 8 weeks.

| Batch/Sample no. | t = 0 SOM230 content (mg/g) | Storage conditions | t = 4 weeks SOM230 content (mg/g) | % of start value | t = 8 weeks SOM230 content (mg/g) | % of start value |
|---|---|---|---|---|---|---|
| B4071S230-1202-05 | 30.5 | 5° C. | 31.1 | 106.0 | 31.0 | 101.8 |
| | | 25° C./60% RH | 31.7 | 104.1 | 30.3 | 99.6 |
| B4071S230-1202-06 | 40.9 | 5° C. | 43.8 | 107.1 | 31.0 | 101.8 |
| | | 25° C./60% RH | 42.8 | 104.6 | 30.3 | 99.6 |
| B4071S230-1202-07 | 50.8 | 5° C. | 53.7 | 105.5 | 51.9 | 102.0 |
| | | 25° C./60% RH | 53.8 | 105.8 | 51.2 | 100.7 |
| B4071S230-1202-08 | 59.9 | 5° C. | 64.2 | 107.2 | 60.7 | 101.3 |
| | | 25° C./60% RH | 63.3 | 105.6 | 61.5 | 102.6 |

TABLE 17

SOM230 purity analysis (by HPLC UV-DAD) of formulations (see
Tables 10 and 14) stored at 5, 25, 40 and 60° C. up to 8 weeks.

| Batch/Sample no. | t = 0 Rel. Area SOM230 (%) | Storage conditions | t = 2 weeks Rel. Area SOM230 (%) | t = 4 weeks Rel. Area SOM230 (%) | t = 8 weeks Rel. Area SOM230 (%) |
|---|---|---|---|---|---|
| B4071S230-1202-01 | 98.9 | 5° C. | — | 98.8 | 98.8 |
| | | 25° C./60% RH | — | 98.4 | 98.3 |
| | | 40° C./75% RH | 98.1 | 96.9 | 96.1 |
| | | 60° C. | 91.4 | 86.2 | — |
| B4071S230-1202-02 | 98.9 | 5° C. | — | 98.7 | 98.8 |
| | | 25° C./60% RH | — | 98.3 | 98.2 |
| | | 40° C./75% RH | 97.9 | 96.8 | 95.4 |
| | | 60° C. | 90.1 | 85.4 | — |
| B4071S230-1202-03 | 99.1 | 5° C. | — | 98.8 | 98.9 |
| | | 25° C./60% RH | — | 98.3 | 97.7 |
| | | 40° C./75% RH | 97.0 | 95.6 | 94.9 |
| | | 60° C. | 90.4 | 85.8 | — |
| B4071S230-1202-04 | 98.6 | 5° C. | — | 98.7 | 98.7 |
| | | 25° C./60% RH | — | 98.3 | 98.1 |
| | | 40° C./75% RH | 98.1 | 96.9 | 96.0 |
| | | 60° C. | 91.3 | 85.7 | — |

TABLE 17-continued

SOM230 purity analysis (by HPLC UV-DAD) of formulations (see Tables 10 and 14) stored at 5, 25, 40 and 60° C. up to 8 weeks.

| Batch/ Sample no. | t = 0 Rel. Area SOM230 (%) | Storage conditions | t = 2 weeks Rel. Area SOM230 (%) | t = 4 weeks Rel. Area SOM230 (%) | t = 8 weeks Rel. Area SOM230 (%) |
|---|---|---|---|---|---|
| 4071S230-1202-109 | 99.1 | 5° C. | — | 99.0 | 99.1 |
|  |  | 25° C./60% RH | — | 98.6 | 98.7 |
|  |  | 40° C./75% RH | 98.5 | 97.6 | 96.3 |
|  |  | 60° C. | 92.9 | 88.3 | — |

TABLE 18

SOM230 purity analysis (by HPLC UV-DAD) of formulations (see Table 11) stored at 5 and 25° C. up to 8 weeks.

| Batch/ Sample no. | t = 0 Rel. Area SOM230 (%) | Storage conditions | t = 4 weeks Rel. Area SOM230 (%) | t = 8 weeks Rel. Area SOM230 (%) |
|---|---|---|---|---|
| B4071S230-1202-05 | 99.0 | 5° C. | 98.8 | 99.0 |
|  |  | 25° C./60% RH | 98.1 | 97.8 |
| B4071S230-1202-06 | 99.0 | 5° C. | 98.8 | 99.0 |
|  |  | 25° C./60% RH | 98.4 | 98.2 |
| B4071S230-1202-07 | 99.1 | 5° C. | 99.1 | 99.2 |
|  |  | 25° C./60% RH | 98.5 | 98.4 |
| B4071S230-1202-08 | 99.1 | 5° C. | 99.0 | 99.2 |
|  |  | 25° C./60% RH | 98.6 | 98.6 |

The following conclusions were drawn based on the peptide content and purity data: No change in SOM230 content or purity at 5° C. was detected (within experimental variability).

Only small changes in the peptide content and purity were detected at 25° C. Depending on formulation type, peptide purity decreased by 2.6-4.2% after 8 weeks at 40° C. with a trend towards decreasing degradation rate with storage time.

A positive effect of the inclusion of EDTA was detected as shown by comparing B4071S230-1202-03 (without EDTA) and 4071S230-1202-109 (with EDTA).

Example 6—In Vivo PK Study III (PK-12-451)

Formulations

Formulations used for in vivo pharmacokinetic (PK) study III in rat (study no. PK-12-451) are outlined in Table 19. The SOM230 concentrations investigated correspond to 40 mg and 50 mg SOM230 free base/mL for the respective formulations. A combination of ethanol (EtOH) and propylene glycol (PG) was used for all formulations. The primary aim was to characterize the PK profiles of the different formulation variants of SOM230 pamoate.

TABLE 19

Lipid/SOM230 formulations selected for PK study III (PK-12-451). Compositions are provided in wt %.

| Batch no. | Test item | SOM230 (pamoate)* | SPC | DOPC | GDO | EtOH | PG |
|---|---|---|---|---|---|---|---|
| B4071S230-1206-09 | 4071S230-H | 5.91 | 39.60 | — | 39.60 | 7.50 | 7.50 |
| B4071S230-1206-10 | 4071S230-I | 7.39 | 38.80 | — | 38.80 | 7.50 | 7.50 |
| B4071S230-1206-11 | 4071S230-J | 5.91 | — | 39.60 | 39.60 | 7.50 | 7.50 |
| B4071S230-1206-12 | 4071S230-K | 5.91 | 39.60 | — | 39.60 | 10.00 | 5.00 |

*The SOM230 pamoate concentration corresponds to 40 mg SOM230 free base/mL for 4071S230-H, -J and -K and 50 mg/mL for 4071S230-I when corrected for peptide purity and content and formulation density.

Manufacturing of the formulations in Table 19 was performed essentially as described in Example 1 with the addition of a sterile filtration step after complete mixing into homogenous liquid formulations. The formulations were sterile filtered under 2.5 bar nitrogen pressure using a PVDF 0.2 micron membrane filter from Millipore.

In Vivo Study Performance

The formulations in Table 19 (PK-12-451) were injected subcutaneously to male Sprague-Dawley rats (body weight ca 330 g) at a dose volume of 0.1 mL per animal (6 mg SOM230/animal) corresponding to 4 and 5 mg SOM230/animal for 4071S230-H, 4071S230-J, 4071S230-K and 4071S230-I, respectively. Blood for pharmacokinetic analysis was collected 1 hour, 6 hours, 1 day, 3 days, 7 days, 14 days, 21 days, 28 days and 35 days after dosing. Blood samples of 0.5 mL were collected by sub-lingual bleeding into EDTA-treated test tubes (Capiject 3T-MQK, Terumo Medical Corporation). The blood was placed on ice immediately after collection and centrifuged (approximately 1500×g, at 5° C. for 10 min) within 30 to 60 minutes. The plasma was transferred into properly labelled translucent 1.5-mL propylene test tubes (Microcentrifuge tubes, Plastibrand, Buch & Holm) and stored below −70° C. until bioanalysis by ELISA assay.

The PK profiles of the respective formulations in Table 19 are provided in FIG. 10.

As is clear from the data in FIG. 9, the PK profiles are generally flat with somewhat higher plasma levels over the first 14 days for 4071S230-I. The Cmax/C28 day plasma concentration ratios varied in the range 2.6-8.4 depending on formulation variant.

A noteworthy result is the fact that the lowest Cmax/C28 day plasma level ratio and hence for this perspective the most attractive PK profile was obtained for 4071S230-J comprising DOPC instead of SPC (see Table 19 for compositions).

The main PK-parameters obtained in PK-12-451 are tabulated in Table 20.

TABLE 20

PK parameters obtained in PK study PK-12-451. Formulation compositions are provided in Table 19.

| Test item | Dose (mg) | Cmax (ng/mL) | C28d (ng/mL) | Cmax/C28d | AUClast (ng/mL * d) |
|---|---|---|---|---|---|
| 4071S230-H | 4.0 | 217.2 ± 52.9 | 40.5 ± 17.6 | 6.0 | 2550 ± 815 |
| 4071S230-I | 5.0 | 352.5 ± 81.8 | 46.0 ± 9.6 | 8.4 | 4211 ± 742 |
| 4071S230-J | 4.0 | 133.6 ± 53.0 | 47.7 ± 21.4 | 2.6 | 2274 ± 630 |
| 4071S230-K | 4.0 | 183.3 ± 55.1 | 40.7 ± 14.2 | 4.9 | 2347 ± 585 |

Example 7—Further Explorative Stability Testing

Summary of Explorative Stability Testing

The compositions of the formulations investigated in the stability study are provided in Table 19. Each formulation was filled in 2R vials with 1.0 g per vial followed by flushing with nitrogen for 5 seconds and closing with Teflon-coated rubber stoppers and aluminium crimp caps. The storage conditions were 5° C. and 25° C./60% RH (ICH compliant). The samples were always allowed to equilibrate for 60 min at ambient RT before start of the HPLC UV-DAD (diode array detection) analysis.

SOM230 Purity Analysis (by HPLC UV-DAD) Up to 12 Weeks

The results from the SOM230 purity analysis after storage up to 12 weeks are presented in FIGS. 10 and 11. No change in the SOM230 purity was detected at 5° C. The total related substances (RS=100%—found peptide purity) observed after 12 weeks at 25° C. was in the range of 1.4-1.9% with the starting values at release (time zero) being in the range from 0.9-1.1%. The SOM230 (pamoate) drug powder was found to contain about 0.7% related substances and hence this level should be taken as the reference level. Adjusted for the SOM230 drug powder reference level, the total related RS, or total degradation products, found after 12 weeks at 25° C. was in the range of 0.7-1.3% whereas the increase of total RS up to 12 weeks, with time zero as reference, was in the range 0.3-0.9% with the DOPC-based formulation (B4071530-1206-11, see Table 19) showing the lowest total RS.

Example 8—Further SOM230 Compositions Comprising DOPC

Lipid formulations of SOM230 comprising DOPC were prepared as described in Example 1 resulting in homogenous liquids after the mixing process. The formulation compositions are provided in Table 21.

TABLE 21

Lipid/SOM230 formulations comprising DOPC. Compositions are provided in wt %.

| Sample no. | SOM230 (pamoate)* | DOPC | GDO | EtOH | PG |
|---|---|---|---|---|---|
| 4071S230-1210-204 | 8.64 | 38.13 | 38.14 | 7.48 | 7.61 |
| 4071S230-1210-205 | 8.65 | 41.97 | 34.42 | 7.49 | 7.47 |
| 4071S230-1210-206 | 8.58 | 34.44 | 41.96 | 7.51 | 7.51 |

*The SOM230 pamoate concentration corresponds to 60 mg SOM230 free base/mL when corrected for peptide purity and content and formulation density.

The formulations (0.2 g) were injected into 5 mL phosphate buffered saline (PBS pH 7.4) using a 1 mL disposable Luer-Lock syringe equipped with a 23G thin wall 16 mm needle. All formulations formed coherent liquid crystal gels in contact with PBS.

Example 9—SOM230 Compositions Comprising DOPC and Different Solvent Content

Lipid formulations of SOM230 comprising DOPC and different solvent content were prepared essentially as described in Example 1 with the addition of a sterile filtration step after complete mixing into homogenous liquid formulations. The formulations were sterile filtered under 2.5 bar nitrogen pressure using a PVDF 0.2 micron membrane filter from Millipore. The formulation compositions are provided in Table 22.

TABLE 22

Lipid/SOM230 formulations comprising DOPC and different solvent content. Compositions are provided in wt %.

| Sample no. | SOM230 (pamoate) | DOPC | GDO | EtOH | PG | SOM230 free base (mg/mL) |
|---|---|---|---|---|---|---|
| B4071S30-1302-13 | 2.94 | 41.0 | 41.0 | 7.5 | 7.5 | 20 |
| B4071S30-1302-14 | 5.82 | 39.6 | 39.6 | 7.5 | 7.5 | 40 |
| B4071S30-1302-15 | 8.65 | 38.2 | 38.2 | 7.5 | 7.5 | 60 |

TABLE 22-continued

Lipid/SOM230 formulations comprising DOPC and different solvent content. Compositions are provided in wt %.

| Sample no. | SOM230 (pamoate) | DOPC | GDO | EtOH | PG | SOM230 free base (mg/mL) |
|---|---|---|---|---|---|---|
| B4071S30-1302-16 | 8.65 | 42.0 | 34.4 | 7.5 | 7.5 | 60 |
| B4071S30-1302-17 | 8.65 | 39.2 | 32.1 | 10.0 | 10.0 | 60 |
| B4071S30-1302-18 | 8.65 | 38.2 | 38.2 | 10.0 | 5.0 | 60 |
| 9-1 | 2.94 | 41.0 | 41.0 | 10.0 | 5.0 | 20 |
| 9-2 | 5.82 | 39.6 | 39.6 | 10.0 | 5.0 | 40 |

The formulations (0.2 g) were injected into 5 mL phosphate buffered saline (PBS pH 7.4) using a 1 mL disposable Luer-Lock syringe equipped with a 23G thin wall 16 mm needle. All formulations formed coherent liquid crystal gels in contact with PBS.

Example 10—High Drug Load SOM230 Compositions

High loading lipid formulations of SOM230 comprising DOPC and different solvent content are prepared essentially as described in Example 1 with the addition of a sterile filtration step after complete mixing into homogenous liquid formulations.

The formulations are sterile filtered under 2.5 bar nitrogen pressure using a PVDF 0.2 micron membrane filter from Millipore. The formulation compositions are provided in Table 23.

TABLE 23

High SOM230 drug load lipid compositions

| Sample no. | SOM230 (pamoate) | DOPC | GDO | EtOH | PG | SOM230 free base (mg/mL) |
|---|---|---|---|---|---|---|
| 10-1 | 13.0 | 33.5 | 33.5 | 10.0 | 10.0 | ca 90 |
| 10-2 | 13.0 | 36.9 | 30.1 | 10.0 | 10.0 | ca 90 |
| 10-3 | 13.0 | 31.0 | 31.0 | 15.0 | 10.0 | ca 90 |
| 10-4 | 13.0 | 34.1 | 27.9 | 15.0 | 10.0 | ca 90 |
| 10-5 | 13.0 | 28.5 | 28.5 | 15.0 | 15.0 | ca 90 |
| 10-6 | 13.0 | 31.4 | 25.6 | 15.0 | 15.0 | ca 90 |

The formulations (0.2 g) are injected into 5 mL phosphate buffered saline (PBS pH 7.4) using a 1 mL disposable Luer-Lock syringe equipped with a 23G thin wall 16 mm needle. All formulations form coherent liquid crystal gels in contact with PBS.

The invention claimed is:

1. A pre-formulation comprising a low viscosity mixture of:
   a) 20-50 wt. % of at least one diacyl glycerol;
   b) 20-54 wt. % of at least one phosphatidyl choline (PC);
   c) 5-15 wt. % ethanol;
   d) 5-15 wt. % propylene glycol;
   e) about 30 mg/ml of at least one peptide somatostatin receptor agonist consisting of pasireotide pamoate, calculated as the free base;
   f) optionally at least one antioxidant;
   wherein the ratio of components a:b is approximately 50:50;
   wherein components c) and d) are present in the pre-formulation in an approximately equal amount;
   wherein the pre-formulation has a viscosity of 1-1000 mPas at 20° C.;
   wherein the pre-formulation forms, or is capable of forming, at least one liquid crystalline phase structure upon contact with excess aqueous fluid.

2. The pre-formulation as claimed in claim 1 wherein component a) comprises glycerol dioleate (GDO).

3. The pre-formulation as claimed in claim 1 wherein component b) comprises soy PC or PC with at least 95% PC head groups and at least 95% C16 to C20 acyl chains having 0 to 3 unsaturations.

4. The pre-formulation as claimed in claim 1 wherein the antioxidant is ascorbic acid, ascorbyl palmitate, EDTA or citric acid.

5. The pre-formulation as claimed in claim 1 wherein the antioxidant is excluded.

6. The pre-formulation as claimed in claim 1 wherein component b) comprises at least one PC selected from the group consisting of DOPC; DPPC, DSPC; MPPC; MSPC; PMPC; POPC; PSPC; SMPC; SOPC; SPPC and mixtures thereof.

7. The pre-formulation as claimed in claim 1 wherein said pre-formulation excludes fragmentation agents.

8. The pre-formulation as claimed in claim 1 wherein component a) is present at a level of 30-40% by weight.

9. The pre-formulation as claimed in claim 1 wherein component b) is present at a level of 30-45% by weight.

10. The pre-formulation as claimed in claim 1 wherein component c) is present at a level of 7.5-10 wt. %.

11. The pre-formulation as claimed in claim 1 wherein components c) and d) combined are present at a total level less than or equal to 25% by weight.

12. The pre-formulation as claimed in claim 1 wherein said pre-formulation has an L2 phase structure.

13. The pre-formulation as claimed in claim 1 wherein GLP-1, GLP-1 analogues and GLP-1 receptor agonists and/or antagonists are not present.

14. The pre-formulation as claimed in claim 1, wherein components c) and d) combined are present at a total level less than or equal to 15-20% by weight.

15. The pre-formulation as claimed in claim 1, wherein component d) is present at a level of 6-12% by weight.

16. The pre-formulation as claimed in claim 1, wherein component d) has a dielectric constant of at least 28 at 25° C.

17. The pre-formulation as claimed in claim 1, wherein:
component a) is present at a level of 30-45 wt. %;
component b) is present at a level of 30-45 wt. %;
component c) is present at a level of 6-10 wt. %;
component d) is present at a level of 6-10 wt. %; and
component e) is present in an amount of about 30 mg/ml.

18. The pre-formulation as claimed in claim 17, wherein:
component a) is present at a level of 33-45 wt. %;
component b) is present at a level of 33-45 wt. %;
component c) is present at a level of 6-10 wt. %;
component d) is present at a level of 6-10 wt. %; and
component e) is present in an amount of about 30 mg/ml.

19. The pre-formulation as claimed in claim 1, wherein:
component a) is present at a level of 30-40 wt. %;
component b) is present at a level of 30-40 wt. %;
component c) is present at a level of 6-10 wt. %;
component d) is present at a level of 6-10 wt. %; and
component e) is present in an amount of about 30 mg/ml.

20. The pre-formulation as claimed in claim 19, wherein:
component c) is present at a level of 7.5-10 wt. %; and
component d) is present at a level of 7.5-10 wt. %.

21. The pre-formulation as claimed in claim 1, wherein:
component a) is present at a level of 38-43 wt. %;
component b) is present at a level of 38-43 wt. %;
component c) is present at a level of 6-10 wt. %;
component d) is present at a level of 6-10 wt. %; and
component e) is present in an amount of about 30 mg/ml.

22. The pre-formulation as claimed in claim 21, wherein:
component c) is present at a level of 7.5-10 wt. %; and
component d) is present at a level of 7.5-10 wt. %.

23. A pre-filled administration device containing the pre-formulation as claimed in claim 1.

24. The device as claimed in claim 23 being a syringe or syringe barrel, a needleless injector, a multi- or single-use injector, a cartridge or a vial.

25. The device of claim 23 containing a single dose of 1 to 200 mg of the peptide somatostatin receptor agonist.

26. The device of claim 23 containing the peptide somatostatin receptor agonist at around 0.2 to 4 mg per day between scheduled administrations.

27. The device of claim 23 containing a total volume for administration of no more than 5 ml.

28. A kit comprising an administration device as claimed in claim 23.

29. A process for the formation of a pre-formulation suitable for the administration of a peptide somatostatin receptor agonist to a subject, said process comprising forming a low viscosity mixture of:
a) 20-50 wt. % of at least one diacyl glycerol;
b) 20-54 wt. % of at least one phosphatidyl choline (PC);
c) 5-15 wt. % ethanol;
d) 5-15 wt. % propylene glycol;
e) about 30 mg/ml of at least one peptide somatostatin receptor agonist consisting of pasireotide pamoate, calculated as the free base;
f) optionally at least one antioxidant;
wherein the ratio of components a:b is approximately 50:50;
wherein components c) and d) are present in the pre-formulation in an approximately equal amount;
and dissolving or dispersing at least one peptide somatostatin receptor agonist in the low viscosity mixture, or in at least one of components a), b), c), d) and optionally f) prior to forming the low viscosity mixture;
wherein the pre-formulation formed has a viscosity of 1-1000 mPas at 20° C.

* * * * *